(12) United States Patent
Poulet et al.

(10) Patent No.: US 10,434,165 B2
(45) Date of Patent: Oct. 8, 2019

(54) FCV RECOMBINANT VACCINES AND USES THEREOF

(71) Applicant: BOEHRINGER INGELHEIM ANIMAL HEALTH USA INC., Duluth, GA (US)

(72) Inventors: Herve Poulet, Sainte Foy-les Lyon (FR); Frédéric Reynard, Saint-Bonnet-de-Mure (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/753,324

(22) PCT Filed: Aug. 16, 2016

(86) PCT No.: PCT/US2016/047187
§ 371 (c)(1),
(2) Date: Feb. 18, 2018

(87) PCT Pub. No.: WO2017/031120
PCT Pub. Date: Feb. 23, 2017

(65) Prior Publication Data
US 2018/0243399 A1    Aug. 30, 2018

Related U.S. Application Data

(60) Provisional application No. 62/207,638, filed on Aug. 20, 2015.

(51) Int. Cl.
*A61K 39/125* (2006.01)
*C12N 7/04* (2006.01)
*A61K 39/12* (2006.01)
*A61K 39/00* (2006.01)

(52) U.S. Cl.
CPC ............ *A61K 39/125* (2013.01); *A61K 39/12* (2013.01); *C12N 7/04* (2013.01); *A61K 2039/5258* (2013.01); *A61K 2039/552* (2013.01); *C12N 2770/32023* (2013.01); *C12N 2770/32034* (2013.01)

(58) Field of Classification Search
None
See application file for complete search history.

(56) References Cited

U.S. PATENT DOCUMENTS

| | | | |
|---|---|---|---|
| 6,224,882 B1 | 5/2001 | Smith | |
| 6,231,863 B1 * | 5/2001 | Colau | C07K 14/005 424/186.1 |
| 6,534,066 B1 | 3/2003 | Poulet | |
| 6,541,458 B1 * | 4/2003 | Audonnet | C07K 14/005 424/184.1 |
| 7,850,978 B2 | 12/2010 | Poulet | |
| 2005/0208073 A1 * | 9/2005 | Poulet | A61K 39/125 424/216.1 |

FOREIGN PATENT DOCUMENTS

WO    WO 2005/080416    *    9/2005
WO    WO2007012944         2/2007

OTHER PUBLICATIONS

Seq ID No. 3 alignment with Geneseq databadse access No. AAB47044 Kruger et al. 2000 in WO200076538.*
Seq ID No. 3 alignment with Geneseq databadse access No. AEB97341 Rong et al. 2005 in WO2005080416.*
Seq ID No. 4 alignment with Geneseq databadse access No. AAB67462 Audonnet et al. 2003 in WO200105934.*
Seq ID No. 4 alignment with Geneseq databadse access No. AEB97341 Rong et al. 2005 in WO2005080416.*
Radford et al. (Veterinary Research. 2007; 38: 319-335).*
Weeks et al. (Research in Veterinary Science. 2001; 71: 223-225).*
Di Martino et al. (Research in Veterinary Science. 2010; 89: 279-281).*
Oers et al. (Journal of Virology. 2015; 96: 6-23).*
McCabe et al., 2005, Vaccine, 23:5380-5388, "Potential for Broad-spectrum protection against feline calicivirus using an attenuated myxoma virus expressing a chimeric FCV capsid protein".
Di Martino et al., 2007, Veterinary Microbiology, 120:173-178, "Assembky if feline calicivirus-like particle and its immunogenicity".
Hervas-Stubbs et al., Journal of Immunology, 2007, 178: 2361-2369, "Insect Baculoviruses Strongly Potentiate Adaptive Immune Responses by Inducing Type I IFN".
Gobar et al., J. AVMA, 2002, 220(10), 1477-1482, "World Wide Web-based survey of vaccination practices, postvaccinal reactions, and vaccine site-associated sarcomas in cats".
Margine et al., Plos One Dec. 2012, vol. 7(12), e51559, "Residual Baculovirus in Insect Cell-Derived Influenza Virus-Like Particle Preparations Enhances Immunogenicity".
Radford et al., Vaccine, 1997, 15(12/13), 1451-1458, "The use of sequence analysis of a feline calicivirus (FCV) hypervariable region in the epidemiological investigation of FCV related disease and vaccine failures".
Burmeister, Wim P., et al. "Structure Determination of Feline Calicivirus Virus-Like Particles in the Context of a Pseudo-Octahedral Arrangement." PLOS ONE, Public Library of Science, journals.plos.org/plosone/article?id=10.1371/journal.pone.0119289.

* cited by examiner

*Primary Examiner* — Shanon A. Foley
(74) *Attorney, Agent, or Firm* — Judy Jarecki-Black; Suzanne Shope

(57) ABSTRACT

The present invention encompasses FCV vaccines or compositions. The vaccine or composition may be a vaccine or composition containing FCV antigens. The invention also encompasses recombinant vectors encoding and expressing FCV antigens, epitopes or immunogens which can be used to protect animals against FCV infection.

17 Claims, 17 Drawing Sheets
Specification includes a Sequence Listing.

Figure 1

| SEQ ID NO: | Type | Gene Description |
|---|---|---|
| 1 | DNA | Codon-optimized DNA encoding FCV capsid protein (125-668) from FCV strain 100869 |
| 2 | DNA | Wild-type DNA encoding FCV capsid protein (125-668) from FCV strain 100869 |
| 3 | Protein | FCV capsid protein (125-668) from FCV strain 100869 |
| 4 | Protein | FCV capsid protein (1-668) from FCV strain 100869 |

Plasmid map pMEB062

Figure 3

Coomassie staining and Western Blot analysis of expressed FCV capsid protein

M: molecular marker
1: supernatant
2: concentrated supernatant

M: molecular marker
1 and 3: supernatant
2 and 4: concentrated supernatant
5: FCV capsid protein positive control Kinetic of infection Expected size: 59kD
T-: wild baculovirus AcNPV Electronic microscopy of FCV VLP Percentage of survival cats per group after the challenge Evolution of the mean rectal temperature after challenge Distribution of the relative daily weight gain per group after challenge

Figure 10

Mean clinical scores per group after challenge

Distribution of the global score per group

Mean FCV Ab titre per group (in $\log_{10}$ OD$_{50}$)

Evolution of viral excretion (in $\log_{10}$ $CCID_{50}$/mL) per group after challenge Distribution of wAuC per group

Figure 15A

```
                1                                                    50
SEQ ID NO:4   (1)  MCSTCANVLKYYDWDPHFRLIINPNKFLSVGFCDNPLMCCYPELLPEFGT
SEQ ID NO:3   (1)  --------------------------------------------------
                51                                                   100
SEQ ID NO:4  (51)  VWDCDQSPQQIYLESILGDDEWSSTYDAIDPVVPPMHWDNAGKIFQPHPG
SEQ ID NO:3   (1)  --------------------------------------------------
               101                                                   150
SEQ ID NO:4 (101)  VLMHYIIGEVSKAWDPNLPLFRLEADDGSITAPEQGTLVGGVIAEPSAQM
SEQ ID NO:3   (1)  -----------------------MADDGSITAPEQGTLVGGVIAEPSAQM
               151                                                   200
SEQ ID NO:4 (151)  SAAADMATGKSVDSEWEAPFSFHTSVNWSTSETQGKILFKQALGFLNPY
SEQ ID NO:3  (28)  SAAADMATGKSVDSEWEAPFSFHTSVNWSTSETQGKILFKQALGFLNPY
               201                                                   250
SEQ ID NO:4 (201)  LTHLAKLYVANSGSIDVRFSISGSGVFGGKLAAIVVPPGVDPVQSTSMLQ
SEQ ID NO:3  (78)  LTHLAKLYVANSGSIDVRFSISGSGVFGGKLAAIVVPPGVDPVQSTSMLQ
               251                                                   300
SEQ ID NO:4 (251)  YPHVLPDARQVEPVVFTIPDLRSTLYHLMSDTDTTSLVIMIYNDLINPYR
SEQ ID NO:3 (128)  YPHVLPDARQVEPVVFTIPDLRSTLYHLMSDTDTTSLVIMIYNDLINPYR
               301                                                   350
SEQ ID NO:4 (301)  NDANSSGCIVTVETKPGSIPKFHLIKPPGSMITHGSVPSDLIPKSSSLWI
SEQ ID NO:3 (178)  NDANSSGCIVTVETKPGSIPKFHLIKPPGSMITHGSVPSDLIPKSSSLWI
               351                                                   400
SEQ ID NO:4 (351)  GNRYWTDITDFVIRPFVFQANRHFDPNQETAGWSTPRFRPITVTISQRGG
SEQ ID NO:3 (228)  GNRYWTDITDFVIRPFVFQANRHFDPNQETAGWSTPRFRPITVTISQRGG
               401                                                   450
SEQ ID NO:4 (401)  EKLGIGIATDFIVPGIPDGWPDTTIPSKLPPAGDYAVTTSNGTDITTPRE
SEQ ID NO:3 (278)  EKLGIGIATDFIVPGIPDGWPDTTIPSKLPPAGDYAVTTSNGTDITTPRE
               451                                                   500
SEQ ID NO:4 (451)  YDSANEIVNNTNFKSMYICGALQRANGDKFISNTAFITTATVEGNNLEFS
SEQ ID NO:3 (328)  YDSANEIVNNTNFKSMYICGALQRANGDKFISNTAFITTATVEGNNLEFS
               501                                                   550
SEQ ID NO:4 (501)  NVINPTKIAVFQDNHVNRDVQTSDVTLALLGYTGIGEEAIGAIRDRVVRI
SEQ ID NO:3 (378)  NVINPTKIAVFQDNHVNRDVQTSDVTLALLGYTGIGEEAIGAIRDRVVRI
               551                                                   600
SEQ ID NO:4 (551)  SVLPETGARGGNHPIPYKNTVKLGYVIRSIDVFNSQILHTSPQISLNNYI
SEQ ID NO:3 (428)  SVLPETGARGGNHPIPYKNTVKLGYVIRSIDVFNSQILHTSPQISLNNYI
               601                                                   650
SEQ ID NO:4 (601)  LPPDSFAVYRIIDANGSWFDIGIDSDGFSFVGVSNIGKLEFPISASYMGI
SEQ ID NO:3 (478)  LPPDSFAVYRIIDANGSWFDIGIDSDGFSFVGVSNIGKLEFPISASYMGI
               651         668
SEQ ID NO:4 (651)  QLAKIRLASNIRSTMTKL
SEQ ID NO:3 (528)  QLAKIRLASNIRSTMTKL
```

Figure 15B

```
              1                                                  50
SEQ ID NO:1  (1)  ATGCCTGACGACGGTTCCATCACCGCTCCCGAGCAGGGCACCCTGGTCGG
SEQ ID NO:2  (1)  ATGGCGGATGACGGTTCCATCACAGCGCCTGAGCAAGGAACGCGGTTGG
              51                                                 100
SEQ ID NO:1  (51) TGGTGTGATCGCCGAGCCCTCCGCTCAGATGTTCCGCTGCTGCTGACATGG
SEQ ID NO:2  (51) AGGAGTCATTGCTGAACCTAGTGCCCAAATGTCAGCGGCCGCTGATATGG
              101                                                150
SEQ ID NO:1  (101) CTACCGCAAGTCCGTGGACCCGAGTGGAGGCTTTCTTCTCCTCCAC
SEQ ID NO:2  (101) CCACAGGTAAAAGCGTTTAACTCTGAGTGGGAGGCGTTCTTTCCTTCCAC
              151                                                200
SEQ ID NO:1  (151) ACCTCCGTGAACTGGTCCACCTCCGAGACCCAGGGCAAGATCCGTCAA
SEQ ID NO:2  (151) ACCAGTGCAACTGGAGTACATCTGAAACCAGGGAAAGATTCCTTTCAA
              201                                                250
SEQ ID NO:1  (201) GCAGGCTCTGGGTCCCCTGCTGAACCCCTACCTGACCCACCTGGCCAAGC
SEQ ID NO:2  (201) ACAGGCCTTAGGGCCCTGGCTAAATCCCTATTCACCCATCTTGCTAAAC
              251                                                300
SEQ ID NO:1  (251) TGTACGTGGCTTGGTCCGGTTCCATCGACGTGCGCTTCTCCATCTCCGGT
SEQ ID NO:2  (251) TATATGTGGCATGGTCCGGCTCTATTGATGTCAGATTCTCTATCTCTGGT
              301                                                350
SEQ ID NO:1  (301) TCGGCTGTTCGGTGGCAAGCTGGCTGTATCGTGGTGCCCCTGGTGT
SEQ ID NO:2  (301) TCGGGTGTGTTCGGTGAAAAGCTTGCACCAATTGTAGTGCCACCAGGGT
              351                                                400
SEQ ID NO:1  (351) GGACCCCGTGCAGTCCACCTCATGCTGCAGTACCCCACGTGCGTTCG
SEQ ID NO:2  (351) GGACCCTGTGCAAAGTACTTCAATGTTGCAGTACCCCATGTTCGTTTG
              401                                                450
SEQ ID NO:1  (401) ACGCTGGTCAGTGGAGCCTGTGTGTTCACCATCCCGACCTGCCTTCC
SEQ ID NO:2  (401) ACGCTGGTCAAGTGGAACCTGTAGTCTTTAGTATCCCTGACCTAAGAAGT
              451                                                500
SEQ ID NO:1  (451) ACCCTGTACCACCTGATGTTCGACACCGACACCACCTCCCTGGGATCAT
SEQ ID NO:2  (451) ACACTTACCACTTAATGTCTGATACTGATACCACCTCCTTAGCCATTAT
              501                                                550
SEQ ID NO:1  (501) GATCTACAACGACCTGATCAACCCCTACGCTAACGACGCTAACCCCTCCG
SEQ ID NO:2  (501) GATTTATAATGACCTAATCAACCCTTATGCTAATGATGCTAATCTTCCGG
              551                                                600
SEQ ID NO:1  (551) GTTCCATCCGTGACCGTGGAGACCAAGCCCGGTTCCGACTTCAAGTTCAT
SEQ ID NO:2  (551) GATGCATAGTCACTGTTGACACTAAACCTGGCTTGATTCAAATTCCAC
              601                                                650
SEQ ID NO:1  (601) CTCCGAAGCCTCCTGGTTCCATGCTGACCCACGGTTCCTGCCCTCCGA
SEQ ID NO:2  (601) CTCTTAAAACCCCGGTTCAATGCTAACACATGGCTCTGTTCCATCTGA
              651                                                700
SEQ ID NO:1  (651) CCTGATCGCCAAGTCCTGTTCCCTGTGCATCGGTAACCGTTACGGACCG
SEQ ID NO:2  (651) CTTGATTGCCAAGTCATCGTCACTATGGATTGGAAACCGCTATGGACTG
              701                                                750
SEQ ID NO:1  (701) ACATCACCGACTTCCTGATCCGGTCCCTTCCTGTTCCAAGCTAACCGTCAC
SEQ ID NO:2  (701) ACATCACTGATTTTCTAATTCGACCATTTCTTTCCAGCGGAATAGGCAC
              751                                                800
SEQ ID NO:1  (751) TTCGACTTCAACCAGCAAACGCTGGTTGGTCAACCCCCGTTCCGTCC
SEQ ID NO:2  (751) TTTGACTTCAATCAGGAGACAGCGGGTGGAGCACTCCTAGGTTTCGGCC
              801                                                850
SEQ ID NO:1  (801) CATCACCGTGACCATCTCCCAGAAGGGTGGCGAGAAGCTGGTATCGGTG
SEQ ID NO:2  (801) AATTACTGTCACCATAAGTCAGAAAGCACGGAAAAGCTCCGAATTCCGA
              851                                                900
SEQ ID NO:1  (851) TCCCTACGACTTCATCCTGCCCGGTATCCCCGACGGTTGCCTGACACC
SEQ ID NO:2  (851) TCCCAACTGACTTTATTGTCCCAGGAATCCTTGATGGTTGGCCAGATACC
```

Figure 15C

```
                          901                                                950
SEQ ID NO:1     (901)     ACCATCCCATTCAAGCTGACCCCCGCTGCTGACTACGCTGTGACCACCTC
SEQ ID NO:2     (901)     ACAATTCCTTCAAAACTGACCCCTGCAGGTGACTACGCAGTCACCACAAG
                          951                                               1000
SEQ ID NO:1     (951)     CAACGGTACTGACATCACCACCCCTCGTGAGTACGACTCCGCTAACGACA
SEQ ID NO:2     (951)     TAATGGACTGACATCACAACATTAAGAGAGTATCATTCGCCTAACGACA
                         1001                                               1050
SEQ ID NO:1    (1001)     TCGTGAACAACACCAACTTCAAGTCCATGTACATCTGCGGTGCTCTGCAG
SEQ ID NO:2    (1001)     TTGTAAACAACACCAATTTTAAAAGCATGTATATATGTCGGGCTTTGCAA
                         1051                                               1100
SEQ ID NO:1    (1051)     CGTCCTTGGCGTGACAAGAAGATCTCCAACACCGCTTTCATCACCACCGC
SEQ ID NO:2    (1051)     AGGCCTGGGGTGATAAGAAAATTTCAAACACTGCTTTCATAACCACTGC
                         1101                                               1150
SEQ ID NO:1    (1101)     TACCGTGGACGGTAACAACTTCGAGCCCTCCAACGTGATCAACCCTACCA
SEQ ID NO:2    (1101)     TACAGTCGAGGGAAATAATCTTGAACCTAGCAATGTGATTAACCCTACAA
                         1151                                               1200
SEQ ID NO:1    (1151)     AGATCGGTGTCTTCAGGACAACCACGTGAACCGTGACGTCAGACCTCC
SEQ ID NO:2    (1151)     AGATTGCCGTGTTCCAAGACAATCATGTTAACGGCGACGTCAAACATCA
                         1201                                               1250
SEQ ID NO:1    (1201)     GACGTGACCCTGGCTCTGCTGGGTTACACCGGTATCGGCGAGGAAGCTAT
SEQ ID NO:2    (1201)     GATGTCACACTGGCTCTCCTTGGCTACACGGGCATTGGTGAAGAAGCAAT
                         1251                                               1300
SEQ ID NO:1    (1251)     CGGTGCTGACCGTGACAAGGTGGTGCCTCATCTCCGTGCTGCCCGAGACCG
SEQ ID NO:2    (1251)     TGGTGCCCACAGAGACAAGGTAGTACGCATTAGTCCTACCTGAGACTG
                         1301                                               1350
SEQ ID NO:1    (1301)     GTGCTCCTGGTGGTAACCACCCCATCTTCTACAAGAACACCGTGAAGCT
SEQ ID NO:2    (1301)     GAGCACGTGGTGGAATCACCCAATCTTTTATAAAAACACCGTGAAATTG
                         1351                                               1400
SEQ ID NO:1    (1351)     GGTTACCTGATCCTTCTATCGACGTGTTCAACTCCCAGATCCTGCACAC
SEQ ID NO:2    (1351)     GGCTATCTAATTAGAAGCATTCATGTGTTCAACTCCAAATTTTGCACAC
                         1401                                               1450
SEQ ID NO:1    (1401)     CTCCCGTCAGCTGTCCTGAACAATACCTGCTGCCCCGACTCCTTCG
SEQ ID NO:2    (1401)     CTCCAGGCAACTTTCTCTTAATAACTATTCTTACCACCTGACTCCTTCG
                         1451                                               1500
SEQ ID NO:1    (1451)     CTGTGTACCGTATCATCGACGCTAACGGTAGCTGCTTCGACATCGGCATC
SEQ ID NO:2    (1451)     CAGTTTATAGAATTATTGATGCTAATGGATCTTGCTTTGATATAGGTATT
                         1501                                               1550
SEQ ID NO:1    (1501)     GACTCCGACGGTTTCTCCTTCGTGGGCCTGTCCAACATCGGCAAGCTCGA
SEQ ID NO:2    (1501)     GATTCAGATGGTTTCTCTTTTGTGGTCTTCTAATATTGGTAAACTTCA
                         1551                                               1600
SEQ ID NO:1    (1551)     GTTCCCCCTGTCCGCTTCCTACATGGGTATCCAGCTGGCTAAGATCCGTC
SEQ ID NO:2    (1551)     GTTTCCTCTCTTGCCTCCTACATGGGAATTCAATTGGCAAAGATTCGGC
                         1601                                               1635
SEQ ID NO:1    (1601)     TGCCTTCAACATCCGTTCCACCATGACCAAGCTC
SEQ ID NO:2    (1601)     TTGCCTCAAACATTAGGAGTACAATGACAAAACTA
```

SEQ ID NO :1 is 75% identical to SEQ ID NO :2

FCV RECOMBINANT VACCINES AND USES THEREOF

CROSS-REFERENCE TO RELATED APPLICATIONS

This application claims priority to U.S. provisional application 62/207,638 filed on Aug. 20, 2015.

FIELD OF THE INVENTION

The present invention relates to compositions for combating feline calicivirus (FCV) infection in animals. The present invention provides pharmaceutical compositions or vaccines comprising an FCV antigen, methods of vaccination against FCV, and kits for use with such methods and compositions.

BACKGROUND OF THE INVENTION

Feline calicivirus (FCV) was first described in 1957 (Fastier L. B., Am. J. Vet. Res., 1957, 18:382-389). Feline calicivirus, and the feline herpesvirus, are the principal sources of viral disease of the upper respiratory tract in domestic cats and wild felids. The FCV affects a large number of animals of the felidae family, with FCV carrying rates of the order of 15 to 20% in clinically healthy domestic cats (Coutts et al., Vet. Rec., 1994, 135:555-556; Ellis T. M., Australian Vet. J., 1981, 57:115-118; Harbour et al., Vet. Rec., 1991, 128:77-80; Reubel et al., Feline Dendistry, 1992, 22:1347-1360). After an initial phase of hyperthermia, these respiratory diseases are generally followed by buccal ulcerations (palate, tongue, lips, nose), rhinitis, conjunctivitis, possibly anorexia and asthenia. The FCV can also cause pneumonia, enteritis, and articular pain (lameness syndrome).

In the last decade, FCV-associated VSD has emerged in the United States of America and the United Kingdom. Several outbreaks have been associated with a high (up to 50%) mortality rate and atypical severe clinical signs (high fever, cutaneous oedema, ulcerative dermatitis and jaundice).

The FCV is transmitted only horizontally, there is no vertical transmission from the mother to its kitten during gestation (Johnson R. P., Res. Vet. Sci., 1984, 31:114-119). FCV is transmitted by contact between infected animals and healthy animals or by the airways during sneezing (Wardley R C., Arch. Virol., 1976, 52:243-249). Feline calicivirus of the caliciviridae family is a non-enveloped virus, with a single-stranded positive RNA (Radfor et al., Proc. 1$^{st}$ Int. Symp., Caliciviruses ESVV, 1997, 93-99). The FCV capsid is constituted with a single major capsidal protein of 66 kDa, the p66 protein. The majority of the commercial FCV vaccines are attenuated vaccines.

A few inactivated vaccines are available. Povey and coworkers (Povey et al., Feline Practice, 1978, 8(3):35-42) describe a formalin inactivated and adjuvanted FCV preparation used in cats. U.S. Pat. Nos. 6,534,066 and 7,850,978 describe the use of new strains of FCV for the production of FCV vaccines. The inactivated vaccines usually contain an adjuvant to improve the immune response and to induce a better protection against heterologous FCV strains emerging in the cat population.

However adjuvanted vaccines induce a higher rate of local adverse reactions than non-adjuvanted ones (Gobar et al., JAVMA, 2002, 220(10), 1477-1482) and thereby increase the risk of vaccine-associated fibrosarcomas at the injection site (Baker R. J., Feline Practice, 1998, 26(5), 18-20).

Non-adjuvanted FCV vaccines are modified live vaccines usually containing the F9 strain. The residual virulence of FCV F9 has been reported by several authors in post-vaccinal calicivirosis (Dawson et al., Vet. Rec. 1993, 132: 346-350). FCV modified live strains are implicated in the emergence of new antigenic variants in the field (Radford et al., Vaccine, 1997, 15(12/13), 1451-1458). The safety of modified live vaccines is therefore questionable.

FCV is a member of the Caliciviridae. It has a 7.7-kb positive-sense RNA genome with three open reading frames (ORFs), encoding the nonstructural protein, the major capsid protein (Carter et al., 1992, Arch. Virol., 122:223-235; Tohya et al., 1997, J. Gen. Virol., 78 (pt. 2), 303-305), and a minor structural protein (Sosnovtsev et al., 2005, J. Virol., 79, 4012-4024). Genetically, FCV strains belong to one diverse genogroup, with little evidence for subspecies clustering. This genetic diversity is accompanied by antigenic diversity, although there is sufficient cross-reactivity that all isolates are deemed to belong to a single serotype.

The capsid proteins from several strains of human calicivirus have been expressed in insect cells infected with recombinant baculoviruses. Virus-like particles have also been produced from the vesivirus feline calicivirus (FCV) by expressing the capsid precursor in a baculovirus expression system (DeSilver et al., 1997, Expression of the complete capsid and the hypervariable region of feline calicivirus in the baculovirus expression system. In: First International Symposium on Caliciviruses. pp. 131-143) where immunization of cats was done with a crude harvest of baculovirus infected insect sf9 cells. The non-inactivated baculovirus has an adjuvant effect (Hervas-Stubbs et al., Journal of Immunology, 2007, 178: 2361-2369; Margine et al., Plos One December 2012|Volume 7|Issue 12|e51559). The insect cells or fractions are used as adjuvants to enhance the immunogenicity of an antigen (U.S. Pat. No. 6,224,882). Di Martino et al. (2007, Vet. Microbiol., 120, 173-178) discuss the expression of FCV capsid VP1 protein in insect cells and the in vitro neutralization of FCV strains using the expressed capsid VP1 protein. However, no in vivo challenge study was done to demonstrate the efficacy of the expressed capsid VP1 protein in cats.

In light of the above, it is apparent that there is a need for vaccines with an improved safety and a good efficacy, including vaccines that are against heterologous FCV strains.

Considering the susceptibility of animals (including humans, albeit rarely) to FCV, a method of preventing FCV infection and protecting animals is essential. Accordingly, there is a need for more effective, stable and safe vaccines against FCV.

SUMMARY OF THE INVENTION

Compositions or vaccines comprising an antigenic FCV polypeptide and fragments and variants thereof are provided. The FCV antigens and fragments and variants thereof possess immunogenic and protective properties. The FCV antigens may be produced by a baculovirus expression vector in insect cells, and assemble into FCV empty capsids or FCV VLPs (virus-like particles).

The antigenic polypeptides and fragments and variants thereof can be formulated into vaccines and/or pharmaceutical compositions. Such vaccines or compositions can be used to vaccinate an animal and provide protection against homologous and heterologous FCV strains.

The present invention demonstrated surprisingly for the first time that the non-adjuvanted compositions or vaccines comprising FCV VLPs, wherein the insect cells were inactivated and cell debris were removed, provided excellent efficacy against a hypervirulent FCV heterologous challenge.

Kits comprising at least one antigenic polypeptide or fragment or variant thereof and instructions for use are also provided.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts a table summarizing the DNA and Protein sequences.

FIG. 3 depicts coomassie staining and Western Blot analysis of expressed FCV capsid protein.

FIG. 10 depicts the mean clinical scores per group after challenge.

FIGS. 15A-C depict the sequence alignments.

DETAILED DESCRIPTION

Figure 2:
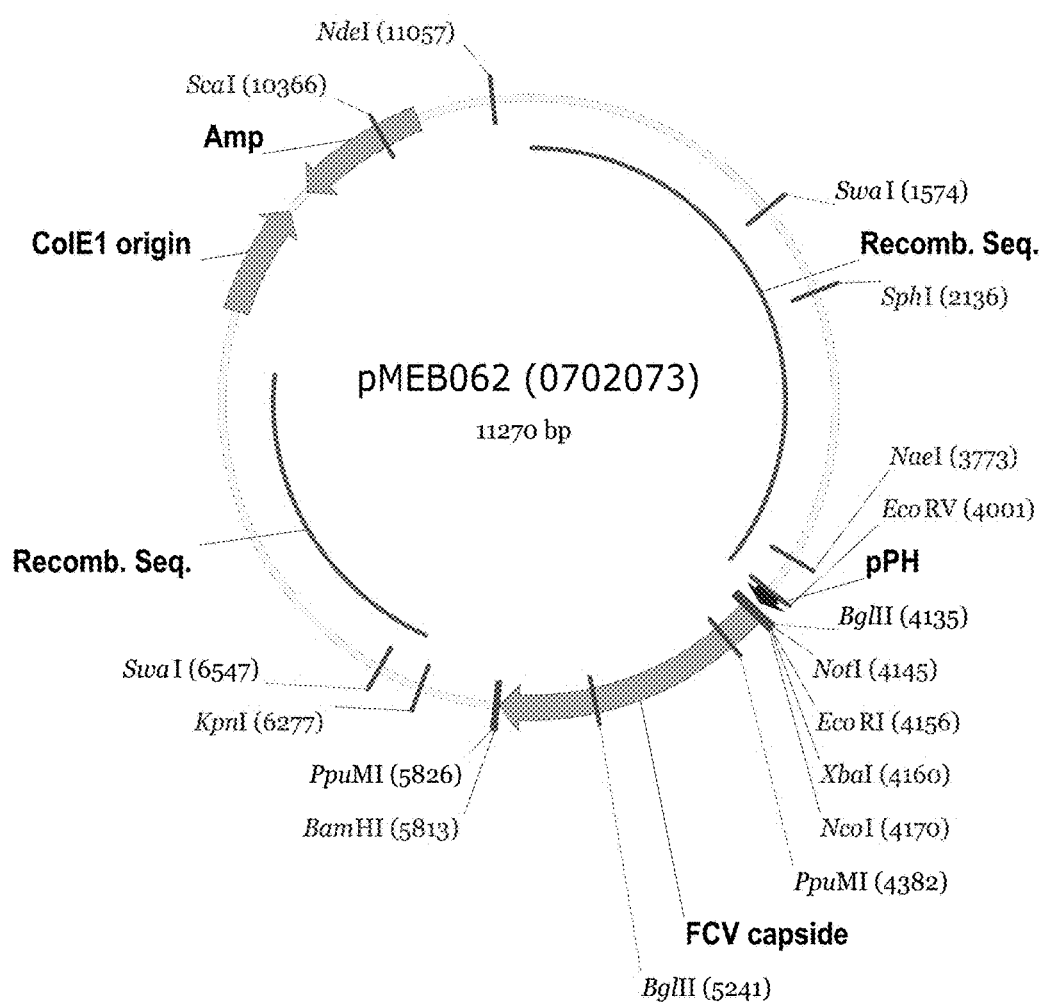
FIG. 2 depicts the plasmid map of pMEB062.

Compositions comprising an FCV polypeptide, antigen and fragments and variants thereof that elicit an immunogenic response in an animal are provided. The antigenic polypeptides or fragments or variants thereof are produced by a baculovirus expression vector in insect cells. The antigenic polypeptides or fragments or variants may be formulated into vaccines or pharmaceutical compositions and used to elicit or stimulate a protective response in an animal. In one embodiment the polypeptide antigen is an FCV capsid polypeptide or active fragment or variant thereof. The FCV antigens may be assembled into FCV empty capsids or FCV VLPs (virus-like particles).

It is recognized that the antigenic polypeptides of the invention may be full length polypeptides or active fragments or variants thereof. By "active fragments" or "active variants" is intended that the fragments or variants retain the antigenic nature of the polypeptide. Thus, the present invention encompasses any FCV polypeptide, antigen, epitope or immunogen that elicits an immunogenic response in an animal. The FCV polypeptide, antigen, epitope or immunogen may be any FCV polypeptide, antigen, epitope or immunogen, such as, but not limited to, a protein, peptide or fragment or variant thereof, that elicits, induces or stimulates a response in an animal, such as an ovine, bovine, caprine or porcine.

The present invention relates to feline or canine vaccines or compositions which may comprise an effective amount of a recombinant FCV antigen. The vaccine or compositions are non-adjuvanted, and may optionally comprise a pharmaceutically or veterinarily acceptable carrier, excipient, or vehicle.

In some embodiments, the response in the animal is a protective immune response.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), swine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

The antigenic polypeptides of the invention are capable of protecting against FCV. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein, polypeptide, or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed the invention encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of an FCV polypeptide. A polynucleotide encoding a fragment of an FCV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding an FCV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. That is the polypeptide is separated from cellular components. By "substantially purified" it is intended that such that the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are FCV antigenic polypeptides that are produced by a baculovirus expression vector in insect cells. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

In one aspect, the present invention provides FCV polypeptides from FCV isolates. In another aspect, the present invention provides a polypeptide having a sequence as set forth in SEQ ID NO:3 or 4, and variant or fragment thereof.

In another aspect, the invention relates to FCV empty capsids or FCV VLPs (virus-like particles).

Moreover, homologs of FCV polypeptides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type FCV polypeptide can differ from the wild-type FCV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type FCV polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the FCV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for FCV polypeptides, the DNA sequence of the FCV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of FCV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the FCV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the FCV polynucleotides contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semi-synthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to ovine, bovine, caprine and porcine vaccines or pharmaceutical or immunological compositions which may comprise an effective amount of a recombinant FCV antigens and a pharmaceutically or veterinarily acceptable carrier, adjuvant, excipient, or vehicle.

The subject matter described herein is directed in part, to compositions and methods related to the FCV antigen prepared in a baculovirus/insect cell expression system that was highly immunogenic and protected animals against challenge from homologous and heterologous FCV strains.

Compositions

The present invention relates to an FCV vaccine or composition which may comprise an effective amount of a recombinant FCV antigen and a pharmaceutically or veterinarily acceptable carrier, excipient, or vehicle. In one embodiment, the recombinant FCV antigen is expressed by a baculovirus expression vector in insect cells.

One embodiment of the invention relates to a vaccine or composition comprising FCV empty capsids or FCV VLPs (virus-like particles). The FCV empty capsids or FCV VLPs (virus-like particles) are obtained by expression of the FCV capsid protein.

The present invention also relates to processes for preparing these vaccines, the use of antigens for producing these vaccines and vaccination methods using them.

The present invention also relates to nucleotide sequences, in particular cDNA, and to amino acid sequences, modified compared with natural sequences of the virus. The invention also relates to the expression products of the modified nucleotide sequences and to the FCV antigens and virus incorporating these modifications.

The present invention encompasses any FCV polypeptide, antigen, epitope or immunogen that elicits an immunogenic response in an animal, such as an ovine, bovine, caprine or swine. The FCV polypeptide, antigen, epitope or immunogen may be any FCV polypeptide, antigen, epitope or immunogen, such as, but not limited to, a protein, peptide or fragment thereof, that elicits, induces or stimulates a response in an animal, such as feline or canine.

In an embodiment wherein the FCV immunological composition or vaccine is a recombinant immunological composition or vaccine, the composition or vaccine comprising a recombinant vector and is non-adjuvated, and may optionally comprise a pharmaceutical or veterinary acceptable excipient, carrier or vehicle; the recombinant vector is a baculovirus expression vector which may comprise a polynucleotide encoding an FCV polypeptide, antigen, epitope or immunogen. The FCV polypeptide, antigen, epitope or immunogen, may be capsid protein and any fragment thereof.

In one embodiment, the nucleic acid molecule encoding one or more FCV antigen(s) is a cDNA encoding a FCV capsid protein. In another embodiment, the nucleic acid molecule encoding one or more FCV antigen(s) is a cDNA encoding a fragment of the FCV capsid protein.

In another embodiment, the FCV antigen may be derived from FCV strain FCV 100869, FCV 431, FCV G1, FCV RMI6, FCV RMI9, FCV 94580, FCV 33585, FCV 89391, and FCV 88287 as described in U.S. Pat. No. 7,850,978, FCV RMI1, FCV RMI2, FCV RMI3, FCV RMI5, FCV RMI6, FCV RMI7, FCV RMI9, FCV A2, FCV F1, FCV G1, FCV G3, FCV F3031, FCV H3-2, FCV H1-4, FCV 431, FCV 388b, FCV 337 and FCV J5 as described in U.S. Pat. No. 6,534,066.

The present invention relates to an FCV composition or vaccine which may comprise an effective amount of a recombinant FCV antigen. The FCV composition or vaccine does not contain an adjuvant. The FCV composition or vaccine may optionally contain a pharmaceutically or veterinarily acceptable carrier, excipient, or vehicle.

The invention further encompasses the FCV polynucleotides contained in a vector molecule or an expression vector and operably linked to a promoter element and optionally to an enhancer.

In one aspect, the present invention provides FCV polypeptides having a sequence as set forth in SEQ ID NO:3 or 4, and variants or fragments thereof.

In another aspect, the present invention provides a polypeptide having at least 70%, at least 75%, at least 80%, at least 85%, at least 90%, at least 95%, 96%, 97%, 98% or 99% sequence identity to an antigenic polypeptide of the invention, particularly to the polypeptides having a sequence as set forth in SEQ ID NO: 3 or 4.

In yet another aspect, the present invention provides fragments and variants of the FCV polypeptides identified above (SEQ ID NO: 3 or 4) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 3 or 4.

An immunogenic fragment of an FCV polypeptide includes at least 8, 10, 15, or 20 consecutive amino acids, at least 21 amino acids, at least 23 amino acids, at least 25 amino acids, or at least 30 amino acids of an FCV polypeptide having a sequence as set forth in SEQ ID NO: 3 or 4, or variants thereof. In another embodiment, a fragment of an FCV polypeptide includes a specific antigenic epitope found on a full-length FCV polypeptide.

In another aspect, the present invention provides a polynucleotide encoding an FCV polypeptide, such as a polynucleotide encoding a polypeptide having a sequence as set forth in SEQ ID NO: 3 or 4. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 3 or 4, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO:1 or 2, or a variant thereof. In yet another aspect, the present invention provides a polynucleotide having at least 70%, at least 75%, at least 80%, at least 85%, at least 90%, at least 95%, at least 95%, 96%, 97%, 98%, or 99% sequence identity to one of a polynucleotide having a sequence as set forth in SEQ ID NO: 1 or 2, or a variant thereof.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an FCV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an FCV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising expression vectors, e.g., therapeutic compositions. The preparations can comprise one or more vectors, e.g., expression vectors, such as in vivo expression vectors, comprising and expressing one or more FCV polypeptides, antigens, epitopes or immunogens. In one embodiment, the vector contains and expresses a polynucleotide that comprises, consists essentially of, or consists of a polynucleotide coding for (and advantageously expressing) an FCV antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an FCV polypeptide, antigen, epitope or immunogen, or a fragment thereof.

According to another embodiment, the vector or vectors in the preparation comprise, or consist essentially of, or consist of polynucleotide(s) encoding one or more proteins or fragment(s) thereof of an FCV polypeptide, antigen, epitope or immunogen, the vector or vectors expressing the polynucleotide(s). In another embodiment, the preparation comprises one, two, or more vectors comprising polynucleotides encoding and expressing, advantageously in vivo, an FCV polypeptide, antigen, fusion protein or an epitope thereof.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an FCV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995.). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter has either a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

The plasmids may comprise other expression control elements. It is particularly advantageous to incorporate stabilizing sequence(s), e.g., intron sequence(s), for example, maize alcohol dehydrogenase intron (Callis et al. Genes & Dev. 1(10):1183-1200, December 1987), the first intron of the hCMV-IE (PCT Application No. WO1989/01036), the intron II of the rabbit β-globin gene (van Ooyen et al., 1979). In another embodiment, the plasmids may comprise 3' UTR. The 3' UTR may be, but not limited to, *agrobacterium* nopaline synthase (Nos) 3' UTR (Nopaline synthase: transcript mapping and DNA sequence. Depicker, A. et al. J. Mol. Appl. Genet., 1982; Bevan, N A R, 1984, 12(22): 8711-8721).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

In one embodiment, the recombinant FCV antigen is expressed in insect cells. In another embodiment, the insect cells are inactivated and cell debris are removed.

Methods of Use

In an embodiment, the subject matter disclosed herein is directed to a method of vaccinating an ovine, bovine, caprine, or swine comprising administering to the ovine, bovine, caprine, or swine an effective amount of a vaccine which may comprise an effective amount of a recombinant FCV antigen and a pharmaceutically or veterinarily acceptable carrier, excipient, or vehicle.

In one embodiment of the present invention, the method comprises a single administration of a vaccine composition formulated with an emulsion according to the invention. For example, in one embodiment, the immunological or vaccine composition comprises baculovirus expressed FCV antigens, including polypeptides and VLPs (virus-like particles) or empty capsids. Electron microscopy indicates the insect cells transformed with baculovirus expression vectors produce FCV VLPs or FCV empty capsids, and so immunological or vaccine compositions according to the instant invention encompass those comprising FCV VLPs or FCV empty capsids.

In an embodiment, the subject matter disclosed herein is directed to a method of vaccinating an ovine, bovine, caprine, or swine comprising administering to the ovine, bovine, caprine, or swine the FCV antigen produced by a baculovirus vector in insect cells.

In an embodiment, the subject matter disclosed herein is directed to a method of eliciting an immune response comprising administering to the ovine, bovine, caprine, or swine a vaccine comprising the FCV antigen produced by a baculovirus vector in insect cells.

In an embodiment, the subject matter disclosed herein is directed to a method of preparing a vaccine or composition comprising isolating an FCV antigen produced by a baculovirus vector in insect cells and optionally combining with a pharmaceutically or veterinarily acceptable carrier, excipient or vehicle. In another embodiment, the method further comprises the steps of inactivating insect cells and removing cell debris.

Both homologous and heterologous FCV strains are used for challenge to test the efficacy of the vaccine. The administering may be subcutaneously or intramuscularly. The administering may be needle free (for example Pigj et or Bioject).

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the boost. This administration protocol is called "prime-boost".

A prime-boost according to the present invention can include a recombinant viral vector is used to express an FCV coding sequence or fragments thereof encoding an antigenic polypeptide or fragment or variant thereof. Specifically, the viral vector can express an FCV gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. Nos. 5,505,941, 5,494,8070), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The FCV antigen of the invention to be expressed is inserted under the control of a specific poxvirus promoter, e.g., the entomopoxvirus *Amsacta moorei* 42K promoter (Barcena, Lorenzo et al. 2000), the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

In another aspect of the prime-boost protocol of the invention, a composition comprising the FCV antigen of the invention is administered followed by the administration of vaccine or composition comprising a recombinant viral vector that contains and expresses the FCV antigen in vivo, or an inactivated viral vaccine (U.S. Pat. Nos. 7,850,978, 6,534,066) or composition comprising the FCV antigen, or a DNA plasmid vaccine or composition that contains or expresses the FCV antigen. Likewise, a prime-boost protocol may comprise the administration of vaccine or composition comprising a recombinant viral vector that contains and expresses an FCV antigen in vivo, or an inactivated viral vaccine or composition comprising an FCV antigen, or a DNA plasmid vaccine or composition that contains or expresses an FCV antigen, followed by the administration of a composition comprising the FCV antigen of the invention. It is further noted that both the primary and the secondary administrations may comprise the composition comprising the FCV antigen of the invention.

A prime-boost protocol comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals based on viral vectors, e.g., non-poxvirus-viral-vector-based compositions, is generally between about 0.1 to about 5.0 ml, between about 0.1 to about 3.0 ml, and between about 0.5 ml to about 2.5 ml.

The efficacy of the vaccines may be tested about 2 to 4 weeks after the last immunization by challenging animals, such as feline or canine, with a virulent strain of FCV, such as the FCV strain 33585.

Further details of these FCV strains may be found on the European Bioinformatics Information (EMBL-EBI) web pages, and all of the associated nucleotide sequences are herein incorporated by reference. The inventors contemplate that all FCV strains, both herein listed, and those yet to be identified, could be expressed according to the teachings of the present disclosure to produce, for example, effective vaccine compositions. Both homologous and heterologous strains are used for challenge to test the efficacy of the vaccines. The animal may be challenged intradermally, subcutaneously, spray, intra-nasally, intra-ocularly, intra-tracheally, and/or orally.

The prime-boost administrations may be advantageously carried out 1 to 6 weeks apart, for example, about 4 weeks apart. According to one embodiment, a semi-annual booster or an annual booster, advantageously using a viral vector-based vaccine or an inactivated FCV vaccine, is also envisaged. The animals are advantageously at least 6 to 8 weeks old at the time of the first administration.

The compositions comprising the recombinant antigenic polypeptides of the invention used in the prime-boost protocols are not adjuvanted, and may optionally be contained in a pharmaceutically or veterinary acceptable vehicle, diluent or excipient. The protocols of the invention protect the animal from FCV and/or prevent disease progression in an infected animal.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

In one embodiment, the invention provides for the administration of a therapeutically effective amount of a formulation for the delivery and expression of an FCV antigen or epitope in a target cell. Determination of the therapeutically effective amount is routine experimentation for one of ordinary skill in the art. In one embodiment, the formulation comprises an expression vector comprising a polynucleotide that expresses an FCV antigen or epitope and a pharmaceutically or veterinarily acceptable carrier, vehicle or excipient. In another embodiment, the pharmaceutically or veterinarily acceptable carrier, vehicle or excipient facilitates transfection or other means of transfer of polynucleotides to a host animal and/or improves preservation of the vector or protein in a host.

In one embodiment, the subject matter disclosed herein provides a detection method for differentiation between infected and vaccinated animals.

It is disclosed herein that the use of the vaccine or composition of the present invention allows the detection of a FCV infection in an animal. It is disclosed herein that the use of the vaccine or composition of the present invention allows the detection of the infection in animals by differentiating between infected and vaccinated animals.

Article of Manufacture

In an embodiment, the subject matter disclosed herein is directed to a kit for performing a method of eliciting or inducing an immune response which may comprise any one of the recombinant FCV immunological compositions or vaccines, or inactivated FCV immunological compositions or vaccines, recombinant FCV viral compositions or vaccines, and instructions for performing the method.

Another embodiment of the invention is a kit for performing a method of inducing an immunological or protective response against FCV in an animal comprising a composition or vaccine comprising an FCV antigen of the invention and a recombinant FCV viral immunological composition or vaccine, and instructions for performing the method of delivery in an effective amount for eliciting an immune response in the animal.

Another embodiment of the invention is a kit for performing a method of inducing an immunological or protective response against FCV in an animal comprising a composition or vaccine comprising an FCV antigen of the invention and an inactivated FCV immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional primo-vaccinations or additional boost-vaccinations.

The following embodiments are encompassed by the invention. In an embodiment, a composition comprising an FCV antigen or fragment or variant thereof and a pharmaceutical or veterinarily acceptable carrier, excipient, or vehicle is disclosed. In another embodiment, the composition described above wherein the FCV antigen or fragment or variant thereof comprises an immunogenic fragment comprising at least 15 amino acids of an FCV antigen is disclosed. In an embodiment, the above compositions wherein the FCV antigen or fragment or variant thereof is partially purified are disclosed. In an embodiment, the above compositions wherein the FCV antigen or fragment or variant thereof is substantially purified are disclosed.

In an embodiment, the above compositions wherein the FCV antigen or fragment or variant thereof is an FCV polypeptide are disclosed. In an embodiment, the above compositions wherein the FCV polypeptide is a capsid protein or a fragment thereof are disclosed. In an embodiment, the above compositions wherein the FCV antigen or fragment or variant thereof has at least 80% sequence identity to the sequence as set forth in SEQ ID NO: 3 or 4 are disclosed. In one embodiment, the above compositions wherein the FCV antigen is encoded by a polynucleotide having at least 70% sequence identity to the sequence as set forth in SEQ ID NO:1 or 2 are disclosed. In another embodiment, a method of vaccinating an animal susceptible to FCV comprising administering the compositions above to the animal is disclosed. In an embodiment, a method of vaccinating an animal susceptible to FCV comprising a prime-boost regime is disclosed. In an embodiment, a substantially purified antigenic polypeptide expressed in insect cells, wherein the polypeptide comprises: an amino acid sequence having at least 80% sequence identity to a polypeptide having the sequence as set forth in SEQ ID NO: 3 or 4 is disclosed. In any embodiment the animal is preferably a feline or canine. In one embodiment, a method of diagnosing FCV infection in an animal is disclosed. In yet another embodiment, a kit for prime-boost vaccination comprising at least two vials, wherein a first vial containing the composition of the present invention, and a second vial containing a composition for the boost-vaccination comprising a composition comprising a recombinant viral vector, or a composition comprising an inactivated viral composition, or a DNA plasmid composition that contains or expresses the FCV antigen is disclosed.

The pharmaceutically or veterinarily acceptable carriers or vehicles or excipients are well known to one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The adjuvants may include a water-in-oil emulsion. Examples of water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil)

and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly) ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.).

Other well-known adjuvants are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In the case of immunological composition and/or vaccine based on a baculovirus/insect cell-expressed polypeptide, a dose may include about 1 μg to about 2000 μg, about 50 μg to about 1000 μg, and from about 100 μg to about 500 μg of FCV antigen, epitope or immunogen. The dose may include about $10^2$ to about $10^{20}$, about $10^3$ to about $10^{18}$, about $10^4$ to about $10^{16}$, about $10^5$ to about $10^{12}$ VLPs. The dose volumes can be between about 0.1 and about 10 ml, between about 0.2 and about 5 ml.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1 Construction and Expression of FCV Capsid Antigens in Baculovirus/Insect Cells System The FCV capsid gene (2007 bp) encodes a 668 amino acid polypeptide composed of propetide (1-124) and capsid protein (mature chain, 125-668). The sequence encoding mature protein (125-668) (SEQ ID NO:3) was cloned and the corresponding DNA sequence was codon-optimized (SEQ ID NO:1) for insect cells. Potential functional domains are shown in table 1 below.

TABLE 1

Potential functional domains_annotated on mature chain (FCV capsid protein/Strain 100869*: 125-668)

| Putative domains | From to (or position) | Length |
|---|---|---|
| Signal peptide | no | / |
| mature chain | 1-545 | 545 |
| Transmembran chain | no | / |
| N-glycosylation sites | 54-170-178-181-229-248-254-332-337-492 | / |

Strain 100869*: FCV strain disclosed in U.S. Pat. No. 7,850,978

Generation of Plasmid pMEB062

The FCV capsid optimized for insect expression (SEQ ID NO:1) was cloned into commercial plasmid pVL1392 (Pharmingen) using the XbaI and Bam HI sites of both the vector and insert to generate the expression plasmid pMEB062 (FIG. 2).

Generation of Recombinant Baculovirus BacMEB062

The baculovirus vector used was AcNPV modified by a lethal deletion which is only rescued through homologous recombination (BaculoGold DNA, Pharmingen).

Plasmid pMEB062 was used to generate a recombinant baculovirus, encoding FCV capsid gene of strain 100869 (U.S. Pat. No. 7,850,978, Merial USA) under control of polyhedrin promoter, by homologous recombination. Spodoptera frugiperda (Sf) 9 insect cells were co-transfected with plasmid pMEB062 and Bsu36I triple-cut linearized AcNPV DNA, according to manufacturer's protocol (Baculogold, Pharmingen). Recombinant baculovirus from co-transfection supernatant were plaque purified twice. Five clones were amplified (passage 1) at 27° C. at a 25 cm² monolayer flask scale. Infected cells and supernatants were analysed for FCV capsid expression by western blot using monoclonals specific to FCV capsid antigen. Clone 3 showed a correct western blot profile. This clone was further amplified (passage 2) at 27° C. at a 50 mL scale in Erlenmeyers (suspension) at 105 rpm. A third passage (passage 3) at a 200 mL scale was performed to obtain virus stock used for protein expression. This virus stock was then titrated by plaque assay. The obtention of the virus stock was performed using SF900II media, supplemented with 2% of FCS. After titration, recombinant baculovirus stock (Passage 3) was used for protein production in serum free medium.

Expression Analysis of Baculovirus BacMEB062

The expected recombinants have the characters as shown in Table 2.

TABLE 2

| Plasmid | Size (AA) | PM (kDa) | Signal peptide | Tag | N-glycosylation | Disulfure bridge | location |
|---|---|---|---|---|---|---|---|
| pMEB062 | 545 | 59.2 | no | no | 10 potential sites | No | secretion |

Insect cells (Sf9) were infected by the generated baculovirus BacMEB062 or by wild-type baculovirus (AcNPV) at a Multiplicity Of Infection (MOI) of 1, 3 and 10 pfu/ml.

Insect cells were grown at 105 rpm in Sf900II medium without FCS during 1 to 4 days at 28° C. Protein production was analyzed by submitting whole Sf9 lysates and culture supernatant to SDS-PAGE (4-20%, Invitrogen) followed by Coomassie Blue staining (Simplyblue SafeStain, Invitrogen) or by western blot with monoclonal antibody against FCV capsid protein.

A band at expected size of 60 kDa is expressed in the supernatant of infected cells as observed by coomassie on FIG. 3 (left panel). The detection of this protein by western blot using a specific monoclonal antibody confirmed the coomassie staining results as indicated in FIG. 3 (right panel).

Figure 4:
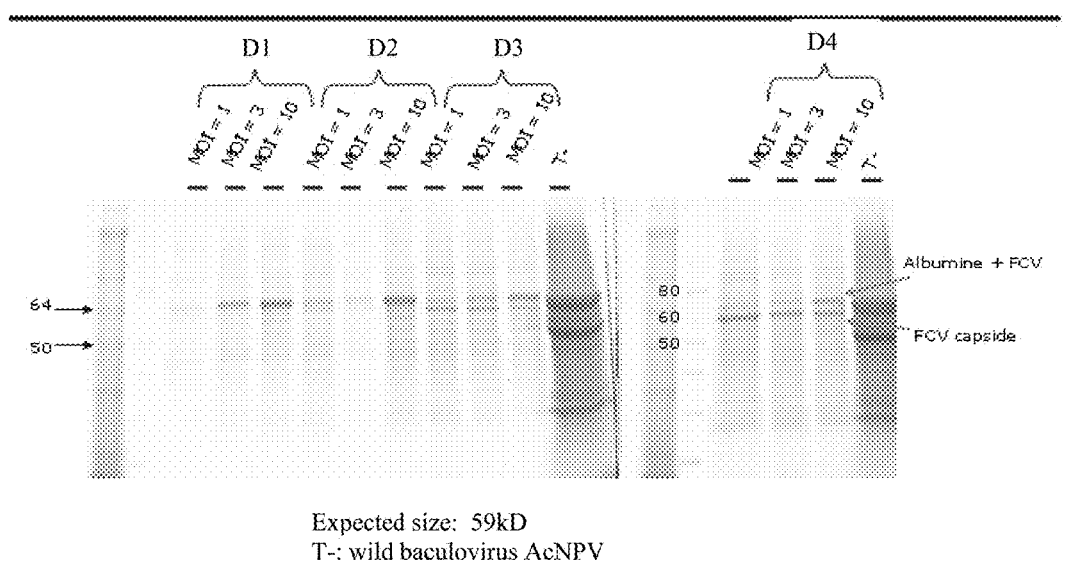
FIG. 4 depicts the kinetic of infection (MOI and days after infection).

Kinetics show that the best conditions for FCV capsid expression are MOI=1 and 4 days post-infection (FIG. 4).

Figure 5:
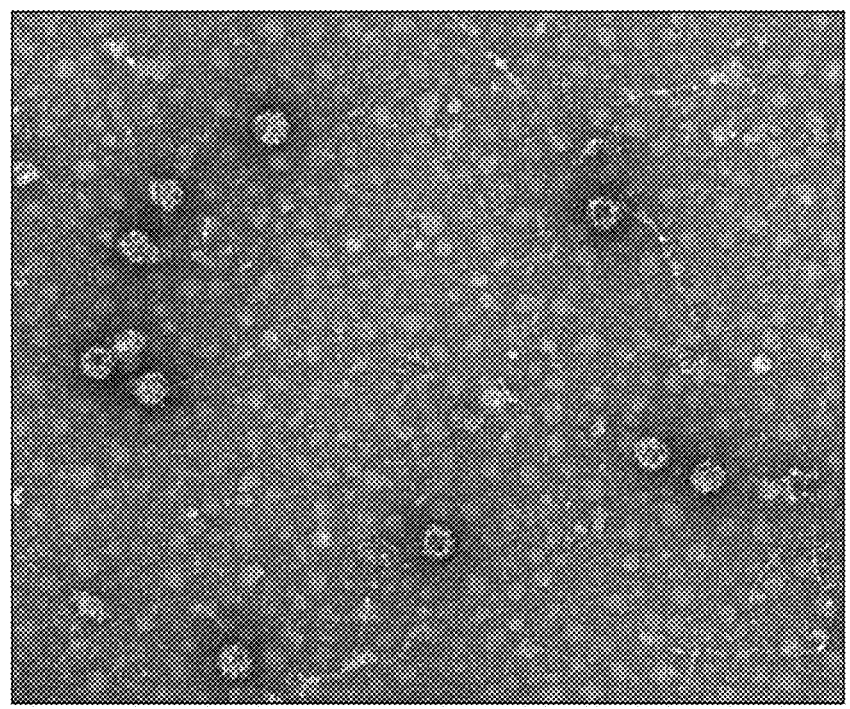
FIG. 5 shows the electronic microscopy of FCV VLP.

The electronic microscopy analysis revealed a correct auto-assembly of the capsid protein into VLPs with a diameter of 40 nm and a correct morphology of calicivirus—like virions at a concentration of $10^{10}$ VLPs/mL (FIG. 5).

In conclusion, baculovirus BacMEB062 generated with transfer plasmid pMEB062 showed good level expression of FCV protein capsid in supernatant and auto-assembling of those proteins into VLPs was proved by electronic microscopy.

Example 2 Vaccination of Cats with Baculovirus Expressed FCV Capsid Protein, and Subsequent Virulent Challenge The objective of this study was to evaluate the efficacy of a feline calicivirus (FCV) virus like particle (VLP) vaccine. VLPs were produced in insect cells infected with a recombinant baculovirus containing the capsid gene of FCV 100869 strain (Example 1). Baculovirus BacMEB062 was grown in Sf9 cells for 7 days (MOI of 0.1). The supernatant harvest was clarified by centrifugation with an in-line disc stack centrifuge to eliminate cell debris. Live baculovirus was partially eliminated by filtration of the supernatant. Remaining live baculoviurus in the supernatant was inactivated by beta-propiolactone (1/300e, 12° C., 24 hours). The efficacy was assessed by challenging cats with a heterologous VS-FCV strain 3 weeks after a primary course of 2 vaccine injections.

The schedule of the study is summarized in Table 3 below.

TABLE 3

Experimental plan

| group | # cat | Treatment D 0 | Treatment D 28 | Challenge D 49 |
|---|---|---|---|---|
| A | 10 | Undiluted FCV VLP 2.5 $10^{10}$ VLPs 2.5 mL by SQ* | Undiluted FCV VLP 2.5 $10^{10}$ VLPs 2.5 mL by SQ | Hypervirulent FCV strain 33585** 1 mL by oro-nasal route |
| B | 10 | 1/10 diluted FCV VLP 2.5 $10^9$ VLPs 2.5 mL by SQ | 1/10 diluted FCV VLP 2.5 $10^9$ VLPs 2.5 mL by SQ | |
| C | 10 | none | none | |

SQ* = subcutaneous route

FCV strain 33585**: Infectious titre $10^{8.5}$ $CCID_{50}$/mL

Volume of one dose of undiluted FCV VLP = 2.5 mL

Volume of one dose of 1/10 diluted FCV VLP (undiluted FCV VLP diluted to 1/10 in PBS without Mg and without Ca) = 2.5 mL A total of 30 SPF cats (14 males and 16 females) were weighed and clinically examined to check their body condition. The cats were 8- to 10-week old on D0. Cats were sequentially assigned to 3 groups of 10 cats (A to C) according to litter, sex and age.

On D3, all animals were weighed. On D0 and D28 a blood sample was collected in dry tubes under general anaesthesia. Sera were stored at −20° C. until titration.

On D0 and D28, each animal of group A received 1 dose of undiluted FCV VLP and each cat of group B received 1 dose of 1/10 diluted FCV VLP by subcutaneous route between the shoulders blades.

The interscapular region was clipped on D3 and disinfected before the injection. Cats from group C were not vaccinated.

From D3 to the day before challenge, clinical examination of cats was performed daily.

On D49, the day of challenge, all the cats were monitored for good general condition. The challenge strain was thawed at 37° C. and diluted to 1/400 in physiological saline buffer (pH 7.1) so as to obtain a suspension titrating about $10^{55}CCID_{50}$/mL, and kept on crushed ice before inoculation.

After general anaesthesia by intramuscular injection), each cat was administered 0.25 mL of diluted challenge strain in each nostril and 0.5 mL orally.

A daily general and local examination was performed on all the animals during a period of 14 days after challenge. The cats were more specifically examined for clinical signs typical of FCV infection as listed in the scoring table 4.

Cats were weighed three days before challenge, then 4, 8, 11 and 14 days post challenge (pc) (i.e. at D46, D53, D57, D60 and D63).

TABLE 4

Clinical score that defines the intensity of the symptoms

| | | Score |
|---|---|---|
| General symptoms | | |
| Rectal temperature (RT) | 37° C. < RT < 39.5° C. | 0 |
| | RT ≥ 39.5° C. | 1 |
| | RT ≤ 37° C. | 2 |
| General condition | Good | 0 |
| | Apathy | 1 |
| | Depression | 2 |
| | Death (or euthanasia for ethical reason) | 20 |
| Dehydration | Absence | 0 |
| | Severe (persistent skin fold) | 1 |
| Weight loss ≥5% between the concerned day and the previous day of weighing | Absence | 0 |
| | Presence | 2 |
| Local symptoms | | |
| Oronasal ulceration | Absence | 0 |
| | Small (<0.4 cm) and few in number (<3) | 1 |
| | Large (≥0.4 cm) and/or numerous (≥3) | 3 |
| Nasal discharge | Absence | 0 |
| | Slight | 1 |
| | Copious | 2 |
| Ocular discharge | Absence | 0 |
| | Presence | 1 |
| Other symptoms | | |
| Facial and/or limb oedema | Absence | 0 |
| | Presence | 3 |
| Skin ulceration/ necrosis | Absence | 0 |
| | Small (<1 cm) and few in number (1 or 2) | 1 |
| | Large (≥1 cm) and/or numerous (≥3) | 3 |
| Icterus | Absence | 0 |
| | Presence | 3 |
| Dyspnoea | Absence | 0 |
| | Presence | 3 |

Pharyngeal swabs were collected the day before challenge and 2, 4, 6, 8, 11 and 14 days pc (i.e., on D47, D51, D53, D55, D57, D60 and D63). They were stored at −70° C. in F15 medium enriched with antibiotics and foetal calf sera (3 mL of growth medium/swab) until viral isolation.

Blood samples were collected in dry tubes the day of challenge (D49) and 14 days later (D63) or on death day under general anaesthesia by intramuscular injection. Sera were stored at −20° C. until titration with FCV antibodies.

FCV antibodies were titrated by ELISA in sera collected at D0, D28, D49 and D63. FCV was isolated and titrated on CrFK (Crandell-Rees Feline Kidney) cells from pharyngeal swabs collected at D51, D53, D57, D60 and D63.

Results

Mortality

Figure 6:
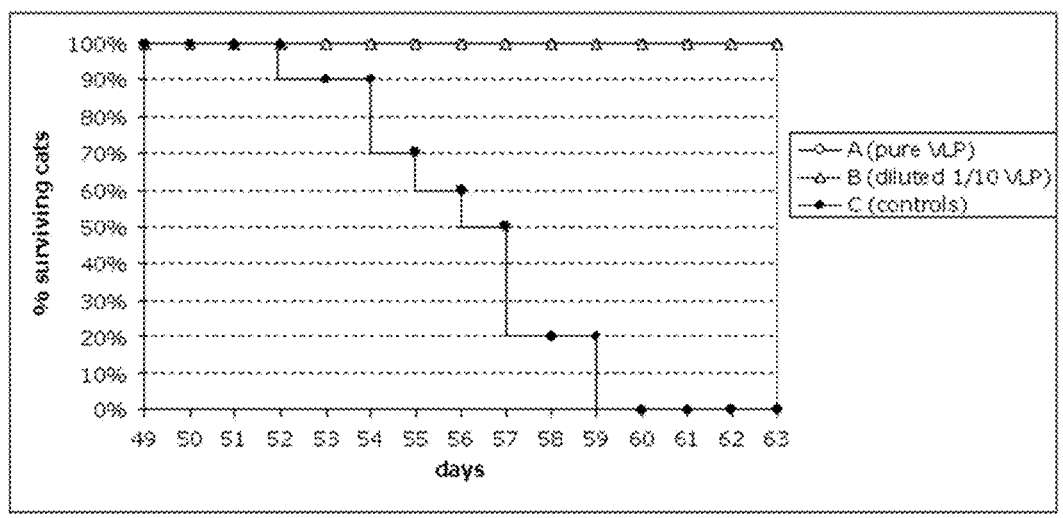
FIG. 6 depicts the percentage of survival cats per group after the challenge.

Mortality results are shown in FIG. 6. The percentage of survival cats after challenge was 100% (10/10) in both vaccinated groups compared to 0% (0/10) in the control group.

After the challenge, none of vaccinated cats died or was euthanized during the monitoring period whereas all controls did, 1 was found dead on day 4 post challenge (pc) (D53), 1 died on day 6 pc (D55) during the clinical examination and 8 were euthanized due to severe clinical symptoms between day 5 and day 11 pc (between D54 and D60).

Temperature

Figure 7:
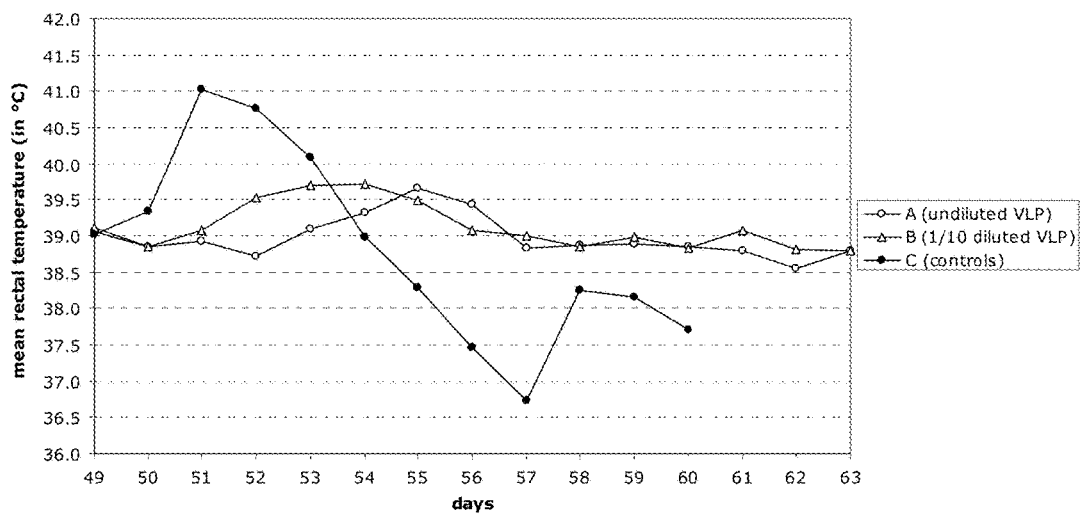
FIG. 7 shows the evolution of the mean rectal temperature after challenge.

FIG. 7 shows the mean rectal temperature after challenge.

In the control group, rectal temperatures increased rapidly and peaked at day 2 pc and then decreased. All controls presented marked hyperthermia (maximal value=41.6° C.). Following the peak of hyperthermia, rectal temperatures decreased and of 10 controls, 5 presented severe hypothermia (RT between 34.5 and 36.8° C.).

After the challenge, rectal temperatures increased slightly in both vaccinated groups until day 7 pc (D56) and then returned to a normal range. Of 10 cats, 4 in group A (undiluted FCV VLP) and 3 in group B (1/10 diluted FCV VLP) did not present any hyperthermia (score for RT=0). Marked hyperthermia (RT>40.0° C.) was observed in 5 out of 10 cats from group A and 4 out of 10 cats from group B (maximal value=41.0° C. in both vaccinated groups).

Figure 8:
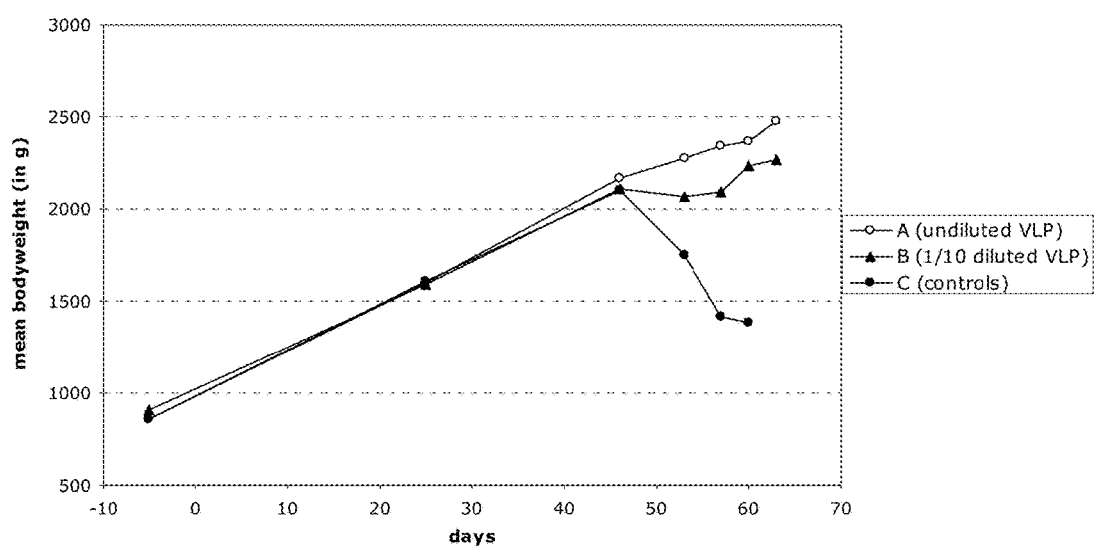
FIG. 8 depicts mean weight per group after challenge.
Figure 9:
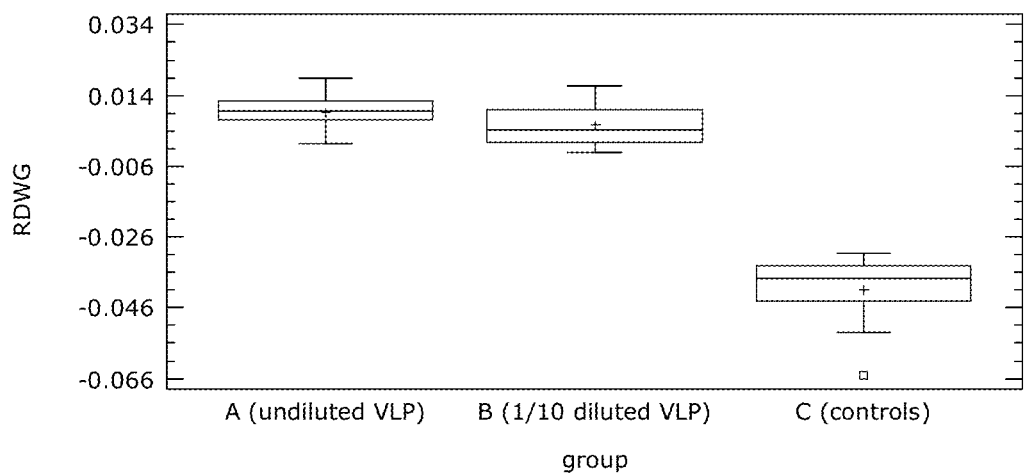
FIG. 9 depicts the distribution of the relative daily weight gain per group after challenge.

The rectal temperature change over time differed significantly (p<0.001) between groups. Two days pc (i.e. on D51, peak of hyperthermia), rectal temperatures were statistically significantly higher in the control group compared to both vaccinated groups (ANOVA, p<0.001). For the D50-D53 period, the temperature was significantly higher in the control group compared to group A (+1.4° C. on average, p<0.001) and to group B (+1.1° C. on average, p<0.001), Weight FIG. 8 shows the mean bodyweight (in g) per group during monitoring period from D5 to D63 (dead cats excluded). FIG. 9 shows the relative mean daily weight gain per group after challenge.

All cats gained weight regularly from D0 to the challenge.

Before challenge (i.e. on D46), there was no significant difference on bodyweight between groups (Kruskal-Wallis, p=0.977).

After challenge, weight loss was observed in all cats from the control group. Controls lost weight until death. The relative daily weight gain was −4% in average. Weight loss was observed in 4/10 cats from group A (undiluted FCV VLP) and 5/10 cats from group B (1/10 diluted FCV VLP). Fourteen days pc, all vaccinated cats reached a weight superior to the initial weight before challenge. The relative weight gain was 1% in average in both vaccinated groups.

The relative daily weight gain was significantly lower in the control groups compared to both vaccinated groups (ANOVA, p<0.001). There was no statistically significant difference on the relative daily weight between the two vaccinated groups.

At 4, 8 and 11 days pc (i.e. D53, D57 and D60), the weight of the control cats were significantly lower than the weight of the cats from groups A and B with a difference ranging on average from 315 g (D53: group B vs. control) to 981 g (D60: group A vs. control).

Whatever the day, no significant difference was observed between the kitten from groups A and B. From D53 through D63, no significant difference was observed between the groups A and B (p=0.250).

Clinical Signs

All controls presented alteration of general condition from day 2 to day 6 pc until death or euthanasia. Apathy was observed in 10/10 controls and depression was observed in 2 cats just before euthanasia.

No alteration of general condition was observed in the vaccinated groups during the monitoring period.

TABLE 5

| | | severe clinical symptoms per group | | | | |
|---|---|---|---|---|---|---|
| Group | # dead | Alteration of general condition (depression) | Copious nasal discharge | Ocular discharge | Face/limb oedema | Dyspnoea |
| A (undiluted FCV VLP) | 0/10 | 0/10 (0/10) | 0/10 | 0/10 | 0/10 | 0/10 |
| B (1/10 diluted FCV VLP) | 0/10 | 0/10 (0/10) | 0/10 | 0/10 | 0/10 | 0/10 |
| C (control) | 10/10 | 10/10 (2/10) | 9/10 | 8/10 | 7/10 | 1/10 | dead: numbers of cats that died or were euthanized following challenge

Global Score

Figure 10:
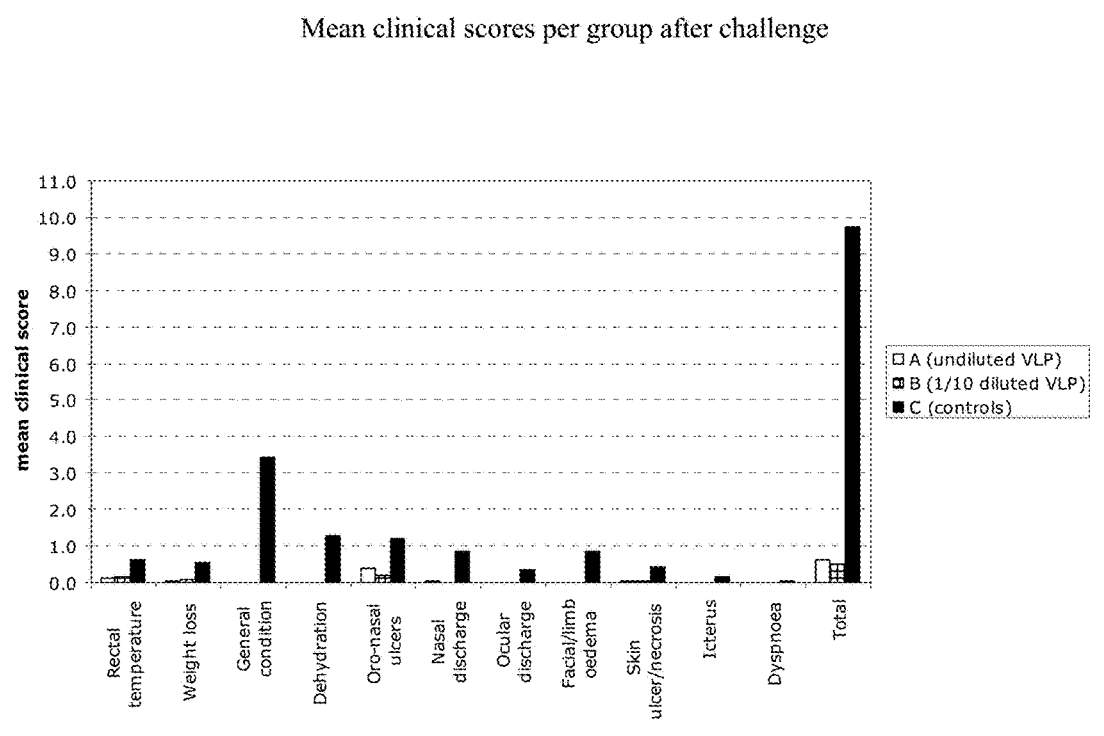
Figure 11:
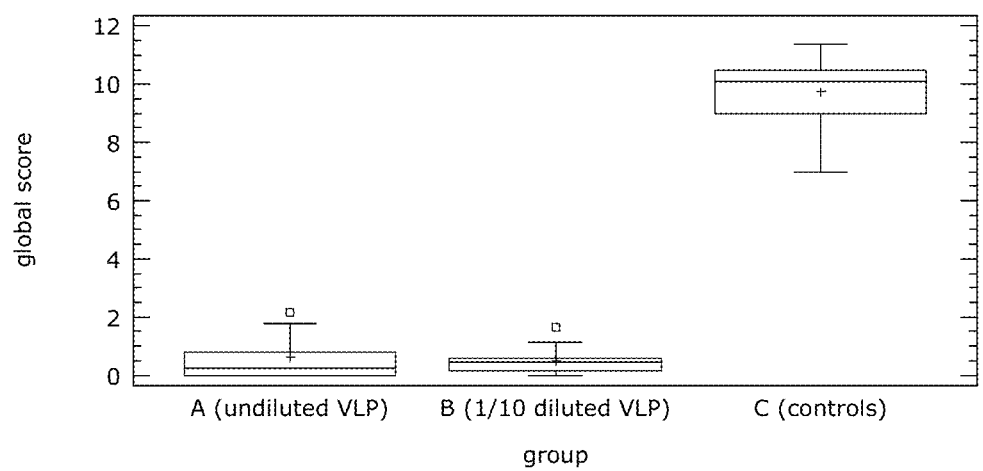
FIG. 11 depicts the distribution of the global score per group.

Clinical scores and their distribution per group after challenge are presented in FIGS. 10 and 11.

The mean global score per group was 0.61 for group A, 0.50 for group B compared to 9.74 for the control group. Of 10 cats, 3 cats from group A and 2 cats from groups B had a global score equal to 0. These cats did not show any clinical sign after challenge.

The global score was statistically significantly reduced in both vaccinated groups compared to the control group (ANOVA, p<0.001). There was no statistically significant difference on the global score between the two vaccinated groups.

FCV Serology

Figure 12:
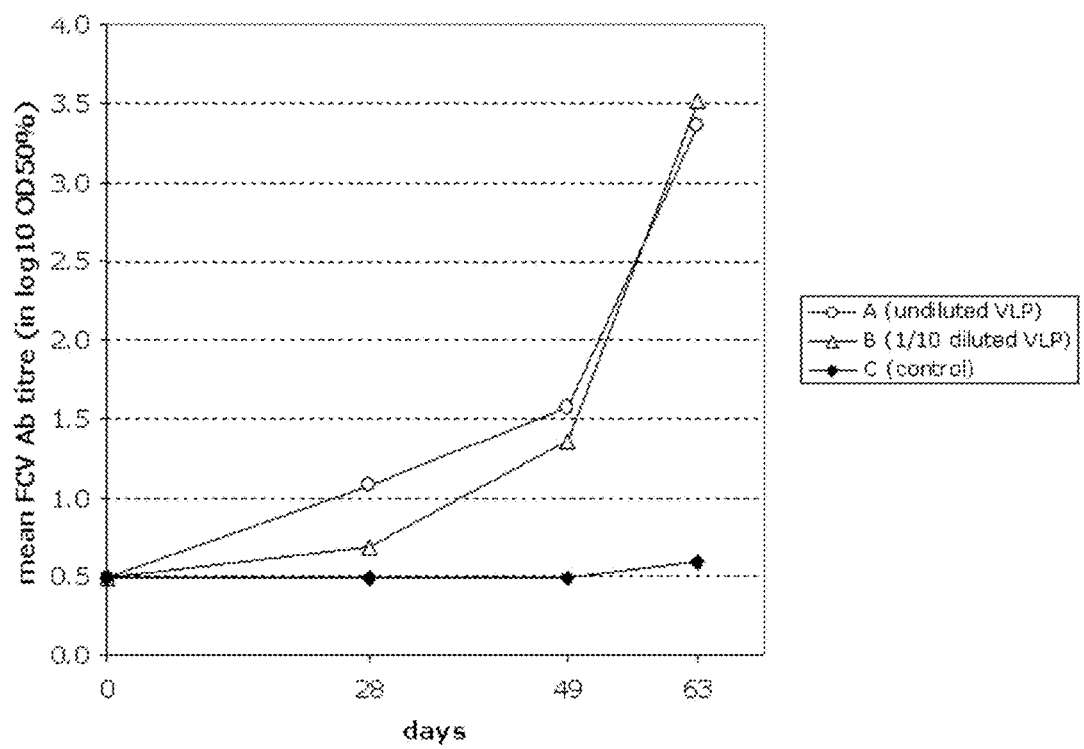
FIG. 12 depicts the mean FCV Ab titre per group (in $\log_{10}$ $OD_{50}$.

FIG. 12 shows the evolution of the mean FCV Ab titre during the monitoring period.

All cats were seronegative for FCV on D0.

A seroconversion was observed in all cats following the first or the second injection of FCV VLPs vaccines. Before the challenge, the mean Ab titre was similar in the vaccinated groups. The FCV challenge induced a booster effect in the vaccinated cats.

All controls remained negative until challenge. Following challenge, only 2 cats that survived till day 11 pc seroconverted. The other cats were still seronegative for FCV at the time of death.

FCV Excretion

Figure 13:
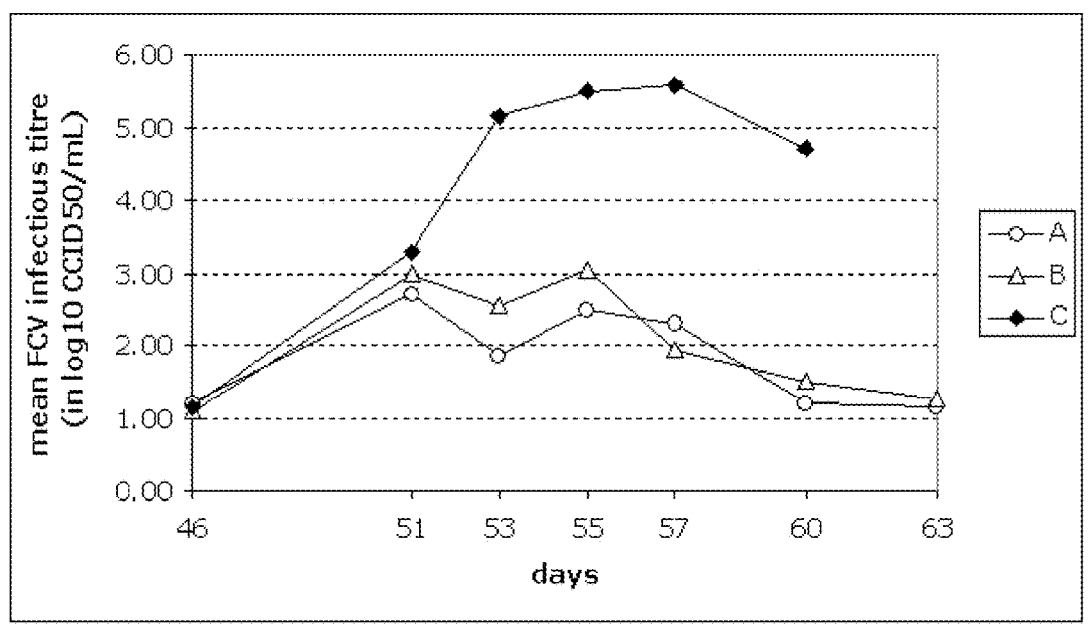
FIG. 13 depicts the evolution of viral excretion (in $\log_{10}$ Cell Culture Infecting $Dose_{50}$/mL) per group after challenge.
Figure 14:
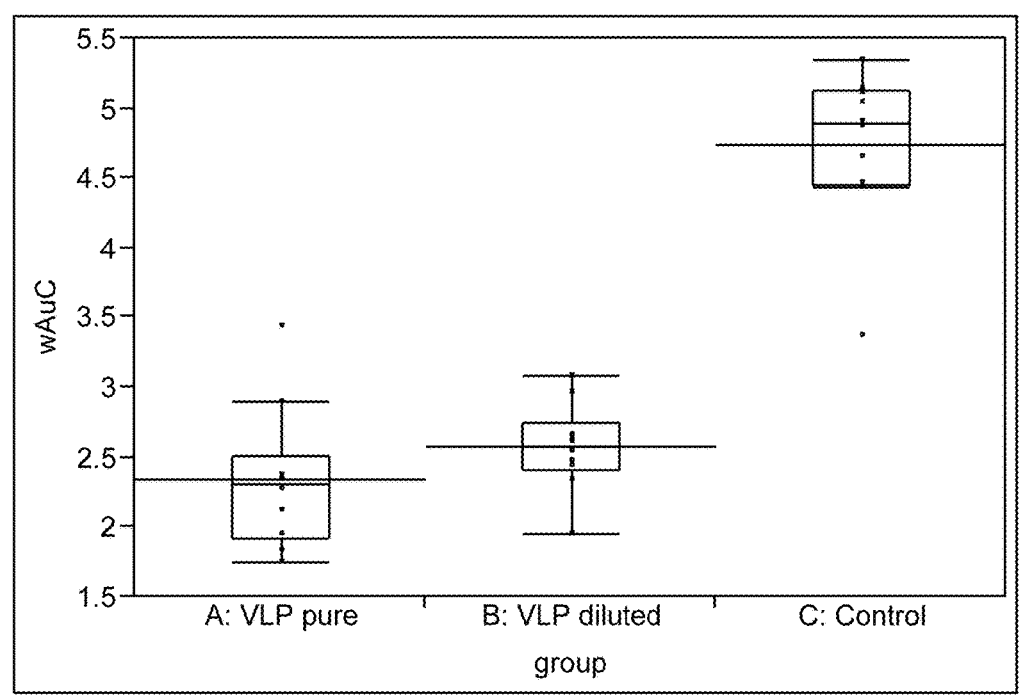
FIG. 14 depicts the distribution of wAuC per group.

FIG. 13 shows the evolution of viral excretion per group after challenge and FIG. 14 shows the wAuC per group.

None of the cats shed virus before challenge.

After challenge, viral excretion increased and peaked on days 2 and 4 pc in groups A and B and then rapidly decreased. Fourteen days pc (i.e. D63), in group A, none of the cats from group A still shed virus, and in group B, only 2 cats still shed virus but at very low quantity (1.2 or 1.7 $\log_{10}$ $CCID_{50}$/mL).

After challenge, all cats from the control group shed virus until death or euthanasia. Titres measured in pharyngeal swabs before death or euthanasia were still high (from 4.2 to 6.2 $\log_{10}$ $CCID_{50}$/mL).

The maximal quantity of FCV excreted ranged from 2.2 to 4.7 $\log_{10}$ $CCID_{50}$/mL in group A, from 3.2 to 4.2 $\log_{10}$ $CCID_{50}$/mL in group B whereas cats from group C excreted a maximum of 5.2 to 6.2 $\log_{10}$ $CCID_{50}$/mL.

On average, there was a significant overall difference between the three treatment groups (p<0.001, ANOVA). Pairwise comparisons showed that the wAuC was higher for cats in the control group than for cats in the group A (p<0.001) and B (p<0.001). No significant difference was observed between groups A and B.

Considering only two vaccinated groups, results from the model show that there was no significant group by day interaction (p=0.373) indicating that the temporal trend did not differ according to the vaccinated group. There was a time effect (p<0.001) but no group effect (p=0.147). Pairwise comparisons show that only at D53, the virus titre was significantly lower in the FCV VLP undiluted group (group A) than in the FCV VLP 1/10 diluted group (group B) (p=0.049).

No difference was observed between the two vaccinated groups when comparing them on the maximum titre and (p=0.173) and on the day at the peak of concentration (p=0.179).

Discussion

Virus-like particles (VLPs) were produced in insect cells infected with a recombinant baculovirus expressing the capsid gene of FCV 100869 strain. This new FCV vaccine was injected to 9-week SPF cats, undiluted (2.5 $10^{10}$ VLPs per dose) or 1/10 diluted (2.5 $10^9$ VLPs per dose), at day 0 and day 28.

The efficacy of this new FCV vaccine was assessed by challenge with an heterologous VS-FCV strain 3 weeks after the $2^{nd}$ vaccination.

All cats were seronegative for FCV before vaccination consistently with their SPF status.

One injection of undiluted or diluted to 1/10 FCV VLP vaccines was sufficient to induce a seroconversion in most cats. Three weeks after the second injection of FCV FCV VLP vaccines, all cats presented ELISA Ab against FCV.

The challenge was validated and very severe. All controls developed FCV typical clinical signs: marked hyperthermia (RT>40.0° C.) for 1 to 3 days at least (10 out of 10), oronasal ulceration (10 out of 10), weight loss (10 out of 10), dehydration (10 out of 10), alteration of body condition (10 out of 10), copious nasal discharge (9 out 10), ocular discharge (8 out of 10), oedema of face or limb (7 out of 10), cutaneous ulceration or necrosis (6 out of 10), icterus (3 out of 10) and dyspnoea (1 out of 10). All oronasal ulcers were large and or numerous except for one cat that presented only small and few ulcers. In addition, one cat was found dead on day 4 pc, one cat died on day 6 pc and 5 cats were euthanized due to the severity of the disease between day 5 and day 11 pc.

In the vaccinated groups, 3 cats injected with undiluted FCV VLP (group A) and 2 cats injected with 1/10 FCV VLP (group B) did not develop any FCV specific symptoms. Clinical symptoms observed in the other vaccinates were less severe than in the control group. Growth was not affected by the challenge.

No alteration of general condition, no copious nasal discharge, no ocular discharge, no face or limb/oedema, no dyspnoea was observed in the vaccinated groups.

No significant difference was observed between undiluted and 1/10 diluted FCV VLP vaccines for the clinical signs.

Following a hypervirulent challenge, both undiluted and 1/10 diluted FCV VLP vaccines prevented cats from death, face or limb oedema, dyspnoea and reduced the frequency and severity of cutaneous necrosis and oro-nasal ulceration.

The challenge induced a booster effect in all vaccinates. In controls, only the 2 cats that survived until day 10 pc developed antibody response that was low.

No dose effect of the FCV VLP vaccines was observed for the clinical signs or the viral shedding.

The study demonstrated that 2 injections of FCV VLP vaccine administered at a dose of 2.5 $10^{10}$ VLPs or 2.5 $10^9$ VLPs 4 weeks apart in 9 weeks old SPF cats significantly reduced severity of clinical signs (prevention from death, face or limb oedema, dyspnoea and reduction of frequency and severity of cutaneous necrosis and oro-nasal ulceration) and significantly reduced viral shedding after a virulent challenge with a heterologous VS-FCV strain.

What we claim is:

1. A composition or vaccine comprising a feline calicivirus (FCV) antigen, wherein the FCV antigen forms FCV VLPs or empty capsids; wherein the FCV antigen comprises a polypeptide having at least 95% sequence identity to the sequence as set forth in SEQ ID NO:3 or 4; wherein the composition or vaccine is not adjuvanted; and wherein the composition or vaccine comprises a pharmaceutically or veterinarily acceptable carrier, excipient, or vehicle.

2. The composition or vaccine of claim 1 wherein the FCV antigen is expressed by a baculovirus vector in insect cells.

3. The composition or vaccine of claim 2, wherein the insect cells are inactivated and cell debris are removed.

4. The composition or vaccine of claim 1, wherein the FCV antigen is a FCV capsid protein.

5. The composition or vaccine of claim 1, wherein the FCV antigen is encoded by a polynucleotide having at least 90% sequence identity to the sequence as set forth in SEQ ID NO:1 or 2.

6. The composition or vaccine of claim 1, wherein the FCV antigen forms FCV VLPs and is expressed by a baculovirus vector in insect cells.

7. The composition or vaccine of claim 6, wherein the insect cells are inactivated and cell debris are removed.

8. A plasmid comprising a polynucleotide encoding an FCV antigen comprising a polypeptide having at least 95% sequence identity to the sequence as set forth in SEQ ID NO: 3 or 4.

9. The plasmid of claim 8, wherein the polynucleotide comprises at least 90% sequence identity to the sequence as set forth in SEQ ID NO:1 or 2.

10. The plasmid of claim 9, wherein the polynucleotide having the sequence as set forth in SEQ ID NO:1 or 2.

11. The plasmid of claim 9 wherein the polynucleotide is operably linked to a promoter.

12. The plasmid of claim 8, wherein the polynucleotide is operably linked to a promoter.

13. The plasmid of claim 8 comprising a polynucleotide encoding an FCV antigen having the sequence as set forth in SEQ ID NO:3 or 4.

14. A stably transformed insect cell expressing FCV empty capsids or FCV VLPs, wherein the insect cell comprises a polynucleotide encoding an FCV antigen comprising a polypeptide having at least 95% sequence identity to the sequence as set forth in SEQ ID NO:3 or 4.

15. The stably transformed insect cell of claim 14, wherein the polynucleotide comprises at least 90% sequence identity to the sequence as set forth in SEQ ID NO:1 or 2.

16. A substantially purified FCV empty capsid or FCV VLP expressed in insect cells, wherein the FCV empty capsid or VLP comprises a polypeptide having at least 95% sequence identity to the sequence as set forth in SEQ ID NO:3 or 4, wherein the insect cells are inactivated and cell debris are removed.

17. A method of vaccinating an animal susceptible to FCV infection or eliciting an immune response in an animal against FCV comprising administering to an animal the composition of claim 1, or the FCV empty capsids or VLPs of claim 16.

* * * * *

SEQUENCE LISTING

<160> NUMBER OF SEQ ID NOS: 4

<210> SEQ ID NO 1
<211> LENGTH: 1635
<212> TYPE: DNA
<213> ORGANISM: artificial sequence
<220> FEATURE:
<223> OTHER INFORMATION: Codon-optimized DNA encoding FCV capsid protein (125-668) from FCV strain 100869-1

<400> SEQUENCE: 1

| | | | | | |
|---|---|---|---|---|---|
| atggctgacg | acggttccat | caccgctccc | gagcagggca | ccctggtcgg | tggtgtgatc | 60 |
| gccgagccct | ccgctcagat | gtccgctgct | gctgacatgg | ctaccggcaa | gtccgtggac | 120 |
| tccgagtggg | aggctttctt | ctccttccac | acctccgtga | actggtccac | ctccgagacc | 180 |
| cagggcaaga | tcctgttcaa | gcaggctctg | gtcccctgc | tgaacccta | cctgaccccac | 240 |
| ctggccaagc | tgtacgtggc | ttggtccggt | tccatcgacg | tgcgcttctc | catctccggt | 300 |
| tccggcgtgt | tcggtggcaa | gctggctgct | atcgtggtgc | ccctggtgt | cgaccccgtg | 360 |
| cagtccacct | ccatgctgca | gtaccccac | gtgctgttcg | acgtcgtca | ggtggagccc | 420 |
| gtggtgttca | ccatcccga | cctgcgttcc | accctgtacc | acctgatgtc | cgacaccgac | 480 |
| accacctccc | tggtgatcat | gatctacaac | gacctgatca | ccccctacgc | taacgacgct | 540 |
| aactcctccg | gttgcatcgt | gaccgtggag | accaagcccg | ttccgactt | caagttccat | 600 |
| ctcctgaagc | tcctggttc | catgctgacc | cacggttccg | tgccctccga | cctgatcccc | 660 |
| aagtcctcct | ccctgtggat | cggtaaccgt | tactggaccg | acatcaccga | cttcgtgatc | 720 |
| cgtcccttcg | tgttccaagc | taaccgtcac | ttcgacttca | ccaggaaac | cgctggttgg | 780 |
| tccaccccc | gtttccgtcc | catcaccgtg | accatctccc | cagaagggtgg | cgagaagctg | 840 |
| ggtatcggta | tcgctaccga | cttcatcgtg | cccggtatcc | ccgacggttg | gcctgacacc | 900 |
| accatcccat | ccaagctgac | ccccgctggt | gactacgctg | tgaccacctc | caacggtact | 960 |
| gacatcacca | ccccctcgtga | gtacgactcc | gctaacgaga | tcgtgaacaa | caccaacttc | 1020 |
| aagtccatgt | acatctgcgg | tgctctgcag | cgtgcttggg | gtgacaagaa | gatctccaac | 1080 |
| accgctttca | tcaccaccgc | taccgtggag | ggtaacaacc | tcgagccctc | caacgtgatc | 1140 |
| aaccctacca | agatcgctgt | gttccaggac | aaccacgtga | accgtgacgt | gcagacctcc | 1200 |
| gacgtgaccc | tggctctgct | gggttacacc | ggtatcggcg | aggaagctat | cggtgctgac | 1260 |
| cgtgacaagg | tggtgcgcat | ctccgtgctg | cccgagaccg | tgctcgtgg | tggtaaccac | 1320 |
| cccatcttct | acaagaacac | cgtgaagctg | ggttacgtga | tccgttctat | cgacgtgttc | 1380 |
| aactcccaga | tcctgcacac | ctcccgtcag | ctgtccctga | caactacct | gctgcccccc | 1440 |
| gactccttcg | ctgtgtaccg | tatcatcgac | gctaacggta | gctggttcga | catcggcatc | 1500 |
| gactccgacg | ttttctcctt | cgtgggcgtg | tccaacatcg | gcaagctcga | gttcccctg | 1560 |
| tccgcttcct | acatgggtat | ccagctggct | aagatccgtc | tggcttccaa | catccgttcc | 1620 |
| accatgacca | agctc | | | | | 1635 |

<210> SEQ ID NO 2
<211> LENGTH: 1635
<212> TYPE: DNA
<213> ORGANISM: artificial sequence
<220> FEATURE:
<223> OTHER INFORMATION: wild-type DNA encoding FCV capsid protein (125-668) from FCV strain 100869-1

<400> SEQUENCE: 2

| | | | | | |
|---|---|---|---|---|---|
| atggcggatg | acggttccat | cacagcgcct | gagcaaggaa | cgctggttgg | aggagtcatt | 60 |
| gctgaaccta | gtgcccaaat | gtcagcggcc | gctgatatgg | ccacaggtaa | aagcgttgac | 120 |
| tctgagtggg | aggcgttctt | tccttccac | accagtgtca | actggagtac | atctgaaacc | 180 |

-continued

```
cagggaaaga ttcttttcaa acaggcctta gggcccttgc taaatcccta tctcacccat    240
cttgctaaac tatatgtggc atggtccggc tctattgatg tcagattctc tatctctggt    300
tcgggtgtgt tcggtggaaa gcttgcagca attgtagtgc caccaggggt cgaccctgtg    360
caaagtactt caatgttgca gtacccccat gttctgtttg acgctcgtca agtggaacct    420
gtagtcttta ctatccctga cctaagaagt acactttacc acttaatgtc tgatactgat    480
accacctcct tagtcattat gatttataat gacctaatca acccttatgc taatgatgct    540
aattcttcgg gatgcatagt cactgttgag actaaacctg gctctgattt caaattccac    600
ctcttaaaac cccccggttc aatgctaaca catggctctg ttccatctga cttgattccc    660
aagtcatcct cactatggat tggaaaccgc tattggactg acatcactga ttttgtaatt    720
cgaccatttg ttttccaggc gaataggcac tttgacttca atcaggagac agcggggtgg    780
agcactccta ggtttcggcc aattactgtc accataagtc agaaaggagg ggaaaagctc    840
ggaattggga tcgcaactga ctttattgtc ccaggaatcc ctgatggttg gccagatacc    900
acaattcctt caaaactgac ccctgcaggt gactacgcag tcaccacaag taatgggact    960
gacatcacaa caccaagaga gtatgattcg gctaacgaga ttgtaaacaa caccaatttt   1020
aaaagcatgt atatatgtgg ggctttgcaa agggcctggg gtgataagaa aatttcaaac   1080
actgctttca taaccactgc tacagtcgag ggaaataatc ttgaacctag caatgtgatt   1140
aaccctacaa agattgccgt gttccaagac aatcatgtta accgcgacgt gcaaacatca   1200
gatgtcacac tggctctcct tggctacacg ggcattggtg aagaagcaat tggtgccgac   1260
agagacaagg tagtacgcat tagtgtccta cctgagactg gagcacgtgg tgggaatcac   1320
ccaatctttt ataaaaacac cgtgaaattg ggctatgtaa ttagaagcat tgatgtgttc   1380
aactcccaaa ttttgcacac ctccaggcaa ctttctctta ataactatct cttaccacct   1440
gactccttcg cagtttatag aattattgat gctaatggat cttggtttga tataggtatt   1500
gattcagatg gtttctcttt tgttggtgtt tctaatattg gtaaacttga gtttcctctc   1560
tctgcctcct acatgggaat tcaattggca aagattcggc ttgcctcaaa cattaggagt   1620
acaatgacaa aacta                                                    1635
```

```

<210> SEQ ID NO 3
<211> LENGTH: 545
<212> TYPE: PRT
<213> ORGANISM: artificial sequence
<220> FEATURE:
<223> OTHER INFORMATION: FCV capsid protein (125-668) from FCV strain
      100869-1

<400> SEQUENCE: 3

Met Ala Asp Asp Gly Ser Ile Thr Ala Pro Glu Gln Gly Thr Leu Val
1               5                   10                  15

Gly Gly Val Ile Ala Glu Pro Ser Ala Gln Met Ser Ala Ala Ala Asp
            20                  25                  30

Met Ala Thr Gly Lys Ser Val Asp Ser Glu Trp Glu Ala Phe Phe Ser
        35                  40                  45

Phe His Thr Ser Val Asn Trp Ser Thr Ser Glu Thr Gln Gly Lys Ile
    50                  55                  60

Leu Phe Lys Gln Ala Leu Gly Pro Leu Leu Asn Pro Tyr Leu Thr His
65                  70                  75                  80

Leu Ala Lys Leu Tyr Val Ala Trp Ser Gly Ser Ile Asp Val Arg Phe
                85                  90                  95
```

-continued

```
Ser Ile Ser Gly Ser Gly Val Phe Gly Lys Leu Ala Ala Ile Val
            100                 105                 110
Val Pro Pro Gly Val Asp Pro Val Gln Ser Thr Ser Met Leu Gln Tyr
        115                 120                 125
Pro His Val Leu Phe Asp Ala Arg Gln Val Glu Pro Val Val Phe Thr
        130                 135                 140
Ile Pro Asp Leu Arg Ser Thr Leu Tyr His Leu Met Ser Asp Thr Asp
145                 150                 155                 160
Thr Thr Ser Leu Val Ile Met Ile Tyr Asn Asp Leu Ile Asn Pro Tyr
                165                 170                 175
Ala Asn Asp Ala Asn Ser Ser Gly Cys Ile Val Thr Val Glu Thr Lys
            180                 185                 190
Pro Gly Ser Asp Phe Lys Phe His Leu Leu Lys Pro Pro Gly Ser Met
        195                 200                 205
Leu Thr His Gly Ser Val Pro Ser Asp Leu Ile Pro Lys Ser Ser Ser
        210                 215                 220
Leu Trp Ile Gly Asn Arg Tyr Trp Thr Asp Ile Thr Asp Phe Val Ile
225                 230                 235                 240
Arg Pro Phe Val Phe Gln Ala Asn Arg His Phe Asp Phe Asn Gln Glu
                245                 250                 255
Thr Ala Gly Trp Ser Thr Pro Arg Phe Arg Pro Ile Thr Val Thr Ile
            260                 265                 270
Ser Gln Lys Gly Gly Glu Lys Leu Gly Ile Gly Ile Ala Thr Asp Phe
        275                 280                 285
Ile Val Pro Gly Ile Pro Asp Gly Trp Pro Asp Thr Thr Ile Pro Ser
        290                 295                 300
Lys Leu Thr Pro Ala Gly Asp Tyr Ala Val Thr Thr Ser Asn Gly Thr
305                 310                 315                 320
Asp Ile Thr Thr Pro Arg Glu Tyr Asp Ser Ala Asn Glu Ile Val Asn
                325                 330                 335
Asn Thr Asn Phe Lys Ser Met Tyr Ile Cys Gly Ala Leu Gln Arg Ala
            340                 345                 350
Trp Gly Asp Lys Lys Ile Ser Asn Thr Ala Phe Ile Thr Thr Ala Thr
        355                 360                 365
Val Glu Gly Asn Asn Leu Glu Pro Ser Asn Val Ile Asn Pro Thr Lys
        370                 375                 380
Ile Ala Val Phe Gln Asp Asn His Val Asn Arg Asp Val Gln Thr Ser
385                 390                 395                 400
Asp Val Thr Leu Ala Leu Leu Gly Tyr Thr Gly Ile Gly Glu Glu Ala
                405                 410                 415
Ile Gly Ala Asp Arg Asp Lys Val Val Arg Ile Ser Val Leu Pro Glu
            420                 425                 430
Thr Gly Ala Arg Gly Gly Asn His Pro Ile Phe Tyr Lys Asn Thr Val
        435                 440                 445
Lys Leu Gly Tyr Val Ile Arg Ser Ile Asp Val Phe Asn Ser Gln Ile
        450                 455                 460
Leu His Thr Ser Arg Gln Leu Ser Leu Asn Asn Tyr Leu Leu Pro Pro
465                 470                 475                 480
Asp Ser Phe Ala Val Tyr Arg Ile Ile Asp Ala Asn Gly Ser Trp Phe
                485                 490                 495
Asp Ile Gly Ile Asp Ser Asp Gly Phe Ser Phe Val Gly Val Ser Asn
            500                 505                 510
Ile Gly Lys Leu Glu Phe Pro Leu Ser Ala Ser Tyr Met Gly Ile Gln
```

```
            515                 520                 525

Leu Ala Lys Ile Arg Leu Ala Ser Asn Ile Arg Ser Thr Met Thr Lys
    530                 535                 540

Leu
545

<210> SEQ ID NO 4
<211> LENGTH: 668
<212> TYPE: PRT
<213> ORGANISM: artificial sequence
<220> FEATURE:
<223> OTHER INFORMATION: FCV capsid protein (1-668)  from FCV strain
      100869-1

<400> SEQUENCE: 4

Met Cys Ser Thr Cys Ala Asn Val Leu Lys Tyr Tyr Asp Trp Asp Pro
1               5                   10                  15

His Phe Arg Leu Ile Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Gln Gln Ile Tyr Leu Glu
    50                  55                  60

Ser Ile Leu Gly Asp Asp Glu Trp Ser Ser Thr Tyr Asp Ala Ile Asp
65                  70                  75                  80

Pro Val Val Pro Pro Met His Trp Asp Asn Ala Gly Lys Ile Phe Gln
                85                  90                  95

Pro His Pro Gly Val Leu Met His Tyr Ile Ile Gly Glu Val Ser Lys
            100                 105                 110

Ala Trp Asp Pro Asn Leu Pro Leu Phe Arg Leu Glu Ala Asp Asp Gly
        115                 120                 125

Ser Ile Thr Ala Pro Glu Gln Gly Thr Leu Val Gly Gly Val Ile Ala
    130                 135                 140

Glu Pro Ser Ala Gln Met Ser Ala Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ala
            180                 185                 190

Leu Gly Pro Leu Leu Asn Pro Tyr Leu Thr His Leu Ala Lys Leu Tyr
        195                 200                 205

Val Ala Trp Ser Gly Ser Ile Asp Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Val Phe Thr Ile Pro Asp Leu Arg
            260                 265                 270

Ser Thr Leu Tyr His Leu Met Ser Asp Thr Asp Thr Thr Ser Leu Val
        275                 280                 285

Ile Met Ile Tyr Asn Asp Leu Ile Asn Pro Tyr Ala Asn Asp Ala Asn
    290                 295                 300

Ser Ser Gly Cys Ile Val Thr Val Glu Thr Lys Pro Gly Ser Asp Phe
305                 310                 315                 320
```

```
Lys Phe His Leu Leu Lys Pro Pro Gly Ser Met Leu Thr His Gly Ser
                325             330             335

Val Pro Ser Asp Leu Ile Pro Lys Ser Ser Leu Trp Ile Gly Asn
            340             345             350

Arg Tyr Trp Thr Asp Ile Thr Asp Phe Val Ile Arg Pro Phe Val Phe
            355             360             365

Gln Ala Asn Arg His Phe Asp Phe Asn Gln Glu Thr Ala Gly Trp Ser
        370             375             380

Thr Pro Arg Phe Arg Pro Ile Thr Val Thr Ile Ser Gln Lys Gly Gly
385             390             395             400

Glu Lys Leu Gly Ile Gly Ile Ala Thr Asp Phe Ile Val Pro Gly Ile
            405             410             415

Pro Asp Gly Trp Pro Asp Thr Thr Ile Pro Ser Lys Leu Thr Pro Ala
            420             425             430

Gly Asp Tyr Ala Val Thr Thr Ser Asn Gly Thr Asp Ile Thr Thr Pro
            435             440             445

Arg Glu Tyr Asp Ser Ala Asn Glu Ile Val Asn Asn Thr Asn Phe Lys
        450             455             460

Ser Met Tyr Ile Cys Gly Ala Leu Gln Arg Ala Trp Gly Asp Lys Lys
465             470             475             480

Ile Ser Asn Thr Ala Phe Ile Thr Thr Ala Thr Val Glu Gly Asn Asn
                485             490             495

Leu Glu Pro Ser Asn Val Ile Asn Pro Thr Lys Ile Ala Val Phe Gln
            500             505             510

Asp Asn His Val Asn Arg Asp Val Gln Thr Ser Asp Val Thr Leu Ala
            515             520             525

Leu Leu Gly Tyr Thr Gly Ile Gly Glu Glu Ala Ile Gly Ala Asp Arg
        530             535             540

Asp Lys Val Val Arg Ile Ser Val Leu Pro Glu Thr Gly Ala Arg Gly
545             550             555             560

Gly Asn His Pro Ile Phe Tyr Lys Asn Thr Val Lys Leu Gly Tyr Val
                565             570             575

Ile Arg Ser Ile Asp Val Phe Asn Ser Gln Ile Leu His Thr Ser Arg
            580             585             590

Gln Leu Ser Leu Asn Asn Tyr Leu Leu Pro Pro Asp Ser Phe Ala Val
        595             600             605

Tyr Arg Ile Ile Asp Ala Asn Gly Ser Trp Phe Asp Ile Gly Ile Asp
        610             615             620

Ser Asp Gly Phe Ser Phe Val Gly Val Ser Asn Ile Gly Lys Leu Glu
625             630             635             640

Phe Pro Leu Ser Ala Ser Tyr Met Gly Ile Gln Leu Ala Lys Ile Arg
                645             650             655

Leu Ala Ser Asn Ile Arg Ser Thr Met Thr Lys Leu
                660             665
```